(12) United States Patent
Eppstein et al.

(10) Patent No.: US 6,922,578 B2
(45) Date of Patent: Jul. 26, 2005

(54) INTEGRATED PORATION, HARVESTING AND ANALYSIS DEVICE, AND METHOD THEREFOR

(75) Inventors: Jonathan A. Eppstein, Atlanta, GA (US); Mark A. Samuels, Norcross, GA (US); Michael R. Hatch, Sugar Hill, GA (US)

(73) Assignees: SpectRx, Inc., Norcross, GA (US); Altea Therapeutics Corporation, Tucker, GA (US)

( * ) Notice: Subject to any disclaimer, the term of this patent is extended or adjusted under 35 U.S.C. 154(b) by 0 days.

(21) Appl. No.: 10/671,006

(22) Filed: Sep. 25, 2003

(65) Prior Publication Data

US 2004/0158137 A1 Aug. 12, 2004

Related U.S. Application Data

(63) Continuation of application No. 09/623,332, filed as application No. PCT/US99/04990 on Mar. 5, 1999, now abandoned.
(60) Provisional application No. 60/077,135, filed on Mar. 6, 1998.

(51) Int. Cl.[7] ............................................... A61B 5/05
(52) U.S. Cl. ...................................................... 600/347
(58) Field of Search ................................ 600/347, 319, 600/316, 365; 604/504, 500, 66, 503, 505

(56) References Cited

U.S. PATENT DOCUMENTS

| | | | | |
|---|---|---|---|---|
| 5,063,081 A | * | 11/1991 | Cozzette et al. ............... 435/4 |
| 5,348,003 A | * | 9/1994 | Caro ........................... 600/310 |
| 5,458,140 A | * | 10/1995 | Eppstein et al. ............. 600/573 |
| 5,708,241 A | * | 1/1998 | Lin ........................... 200/16 C |
| 5,708,247 A | * | 1/1998 | McAleer et al. ........ 204/403.05 |
| 5,800,373 A | * | 9/1998 | Melanson et al. ............. 602/52 |
| 5,885,211 A | * | 3/1999 | Eppstein et al. ............. 600/309 |
| 6,040,194 A | * | 3/2000 | Chick et al. ................. 436/501 |

* cited by examiner

Primary Examiner—Daniel Robinson
(74) Attorney, Agent, or Firm—Altera Law Group, LLC

(57) ABSTRACT

An integrated device for poration of biological tissue, harvesting a biological fluid from the tissue, and analysis of the biological fluid. The device comprises a tissue-contacting layer having an electrically or optically heated probe to heat and conduct heat to the tissue to form at least one opening, such as a micropore to collect biological fluid from the opening, and a detecting layer responsive to the biological fluid to provide an indication of a characteristic of the biological fluid, such as the concentration of an analyte in interstitial fluid. In the embodiment in which, the probe comprises a photosensitizing assembly designed for the uniform application of a photosensitizing material, such as, for example, a dye or a pigment, to a tissue, e.g., the stratum corneum. In one embodiment, the photosensitizing assembly comprises photosensitizing material combined with a carrier, such as, for example, an adhesive or an ink, and the resulting combination is applied to a substrate, such as, for example, an inert polymeric substrate to form a photosensitizing assembly. In another embodiment, the photosensitizing assembly comprises photosensitizing material incorporated into a film-forming polymeric material.

52 Claims, 19 Drawing Sheets

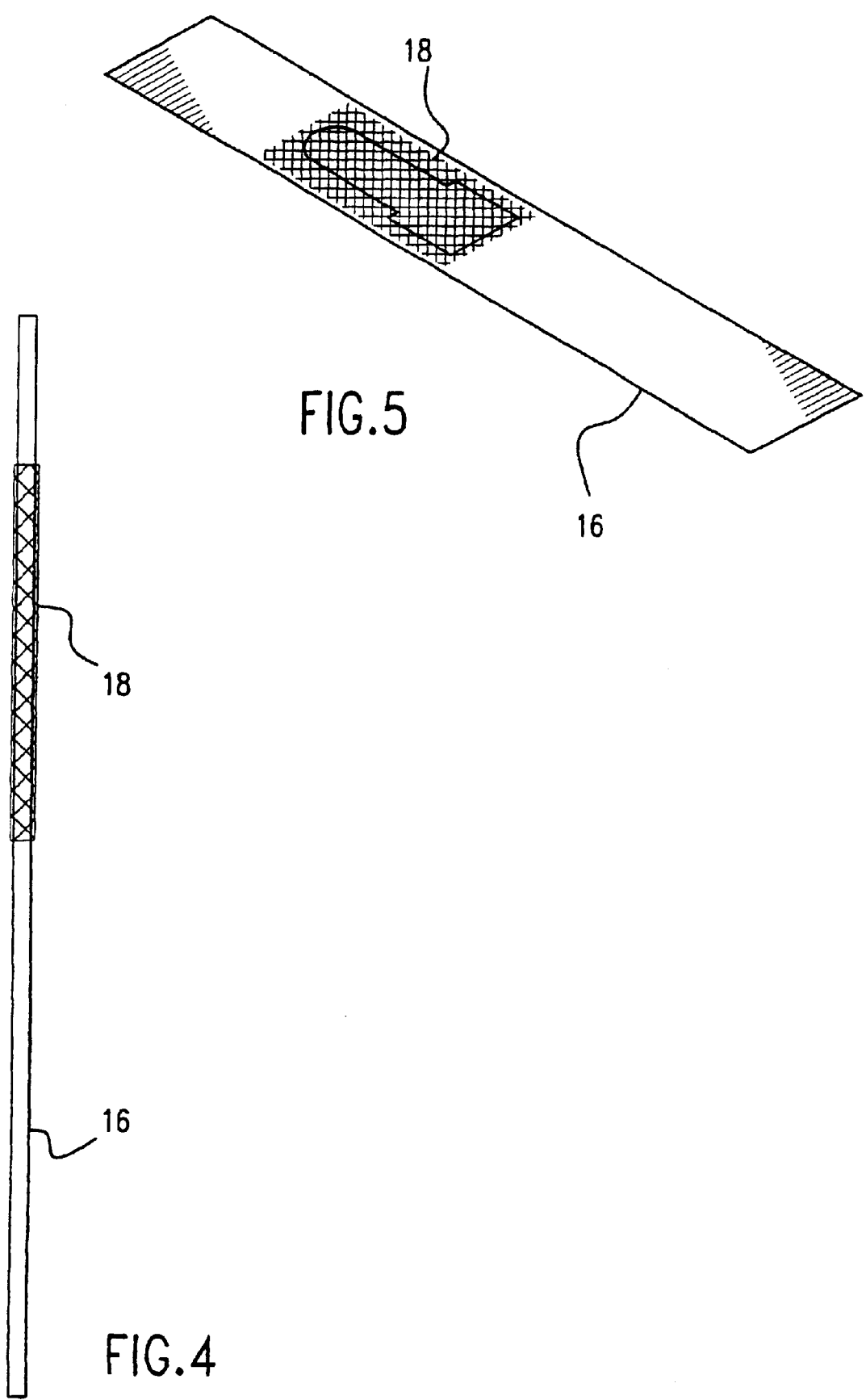

INTEGRATED PORATION, HARVESTING AND ANALYSIS DEVICE, AND METHOD THEREFOR

This application is a continuation of Ser. No. 09/623,332 filed Nov. 6, 2000 now abandoned, which is a 371 of PCT/US99/04990 filed Mar. 5, 1999, which claims benefit of Ser. No. 60/077,135 filed Mar. 6,1998.

BACKGROUND OF THE INVENTION

1. Field of the Invention

This invention relates to an integrated device for the creation of micropores in tissue, the harvesting of a biological fluid from the tissue, and the monitoring or analysis of a characteristic of the biological fluid, such as the concentration of an analyte.

2. Discussion of the Art

The prevalence of diabetes has been increasing markedly in the world. At this time, diagnosed diabetics represent approximately 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the bloodstream. Proper maintenance of the level of glucose in the bloodstream may prevent and even reverse many of the effects of diabetes.

Traditional glucose monitoring devices operate on the principle of taking blood from an individual by a variety of methods, such as by needle or lancet. An individual applies a drop a blood to a strip which contains chemistry that interacts with the blood. The strip is inserted into a blood-glucose meter for measurement of glucose concentration based on a change in reflectance of the strip.

These prior art glucose monitoring systems require that an individual have separately available a needle or lancet for extracting blood, strips carrying blood chemistry for creating a chemical reaction with respect to the glucose in the blood stream and changing color, and a blood-glucose meter for reading the change in color indicating the level of glucose in the bloodstream. The level of blood glucose, when measured by a glucose meter, is read from a strip carrying the blood chemistry through a well-known process.

Generally lancets comprise a blade and a trigger button. The blade has an acute end capable of piercing skin. By striking the trigger button, the acute end of the blade will pierce the skin, for example, of the finger. The finger lancet is primarily used to obtain small volumes of blood, i. e., less than 1 mL. Diabetics use the finger lancet to obtain volumes of blood less than 25 $\mu$L for glucose analysis. There are many small blood vessels in each finger so that a finger can be squeezed to produce a larger drop of blood. In addition, the finger is one of the most sensitive parts of the body; accordingly, the finger lancet causes more pain than what would be experienced by extracting blood via a lancet at a different body site. The finger lancet presents another problem due to the limited area available on the fingers. Diabetics typically monitor blood glucose levels two to four times per day, and consequently must repeat lancing of areas that are still healing. Because fingers are sensitive to pain, there has been a recent trend to subject the arm to blood sampling. See, for example, U.S. Pat. No. 4,653,513 which discloses a device comprising a cylindrical housing, a lancet support, and a gasket or flexible portion slidably accommodated in the housing. Springs retract the lancet support to thereby reduce air pressure in the housing so that it automatically sucks a blood sample immediately after a lancet pierces the skin.

There are other technologies being developed to provide an alternative to the conventional blood glucose monitoring procedures. One such technology involves measuring the level of glucose in interstitial fluid. In order to obtain samples of interstitial fluid, the barrier function of the stratum corneum must be overcome.

U.S. patent application Ser. No. 08/776,863 entitled "Microporation Of Human Skin For Drug Delivery and Monitoring Applications," filed Feb. 7, 1997, to Eppstein et al., discloses a method of ablating the stratum corneum to form at least one micropore comprising the steps of treating a selected area of the stratum corneum with an effective amount of dye that exhibits strong absorption over the emission range of a pulsed light source and thermally ablating the stratum corneum by optically heating the dye. Heat is conductively transferred by the dye to the stratum corneum to elevate the temperature of tissue-bound water and other vaporizable substances in the selected area above the vaporization point of water and other vaporizable substances. Another microporation technique disclosed in that application which involves the use of a solid thermal probe that is applied directly to the tissue. To the subject, these techniques are much less painful than using a lancet, if not completely painless.

There is room for improving on these glucose monitoring technologies. In particular, it is desirable to integrate several functions of the glucose monitoring procedure onto a single device. Preferably, this device would facilitate the harvesting of a biological fluid, such as interstitial fluid, the collection and management of the interstitial fluid, and the analysis of the interstitial fluid to determine a measure of a characteristic of the fluid, such as glucose level.

SUMMARY OF THE INVENTION

Briefly, the present invention is directed to a device for porating tissue, harvesting of a biological fluid from the tissue, such as interstitial fluid, and analysis of the biological fluid. The device is a multi-layer device comprising a tissue-contacting layer, a fluid-transporting layer, and a meter-interface layer. To facilitate harvesting of interstitial fluid, a heated probe is included on the tissue-contacting layer of the device. The heated probe may be heated by electrical current, or by other electromagnetic energy, such as optical energy. In either case, the heated probe heats up and transfers thermal energy by conduction to the tissue to which the device is applied, such as skin. The tissue is ablated so as to form at least one opening or micropore therein. Interstitial fluid, or if the opening is deep enough, blood, is collected from the opening formed in the tissue. A detecting layer on the meter-interface layer detects a characteristic of the fluid, such as the concentration of an analyte. In addition, an optional fluid-transporting layer is provided to facilitate the flow of fluid to the detecting layer.

The poration of tissue, harvesting and analysis of a biological fluid may be enhanced by the application of several mechanisms, including, but not limited to, the application of negative pressure to the porated site, and the application of mechanical force to bulge the tissue into the integrated device, and the application of sonic energy.

Furthermore, the present invention is directed to a device and method for the uniform application of a photosensitizing material, such as, for example, a dye or a pigment, to a tissue, e.g., the stratum corneum, for the purpose of photothermal treatment of the tissue. In one embodiment, the photosensitizing assembly comprises a photosensitizing material that is combined with a carrier, such as, for example, an adhesive or an ink, and the resulting combination is applied to a substrate, such as, for example, an inert polymeric substrate to form a photosensitizing assembly. Means of application of the photosensitizing material to the carrier include, but are not limited to, printing, spraying, and casting. In another embodiment of a photosensitizing assembly, the photosensitizing material may be incorporated into a film-forming polymeric material, and the resulting mixture can then be processed to form a film. The photosensitizing assembly of either embodiment is placed in contact with the tissue, e. g., the stratum corneum, and illuminated with a light source, such as a laser.

The above and other objects and advantages of the present invention will become more readily apparent when reference is to made to the following description, taken in conjunction with the accompanying drawings.

BRIEF DESCRIPTION OF THE DRAWINGS

FIG. 4 is a side view of an overcoat layer and fluid-transporting layer of the device shown in FIGS. 1–3.

FIG. 5 is a perspective view of the overcoat layer and fluid-transporting layer shown in FIG. 4.

DETAILED DESCRIPTION OF THE DRAWINGS

Definitions

Figure 1:
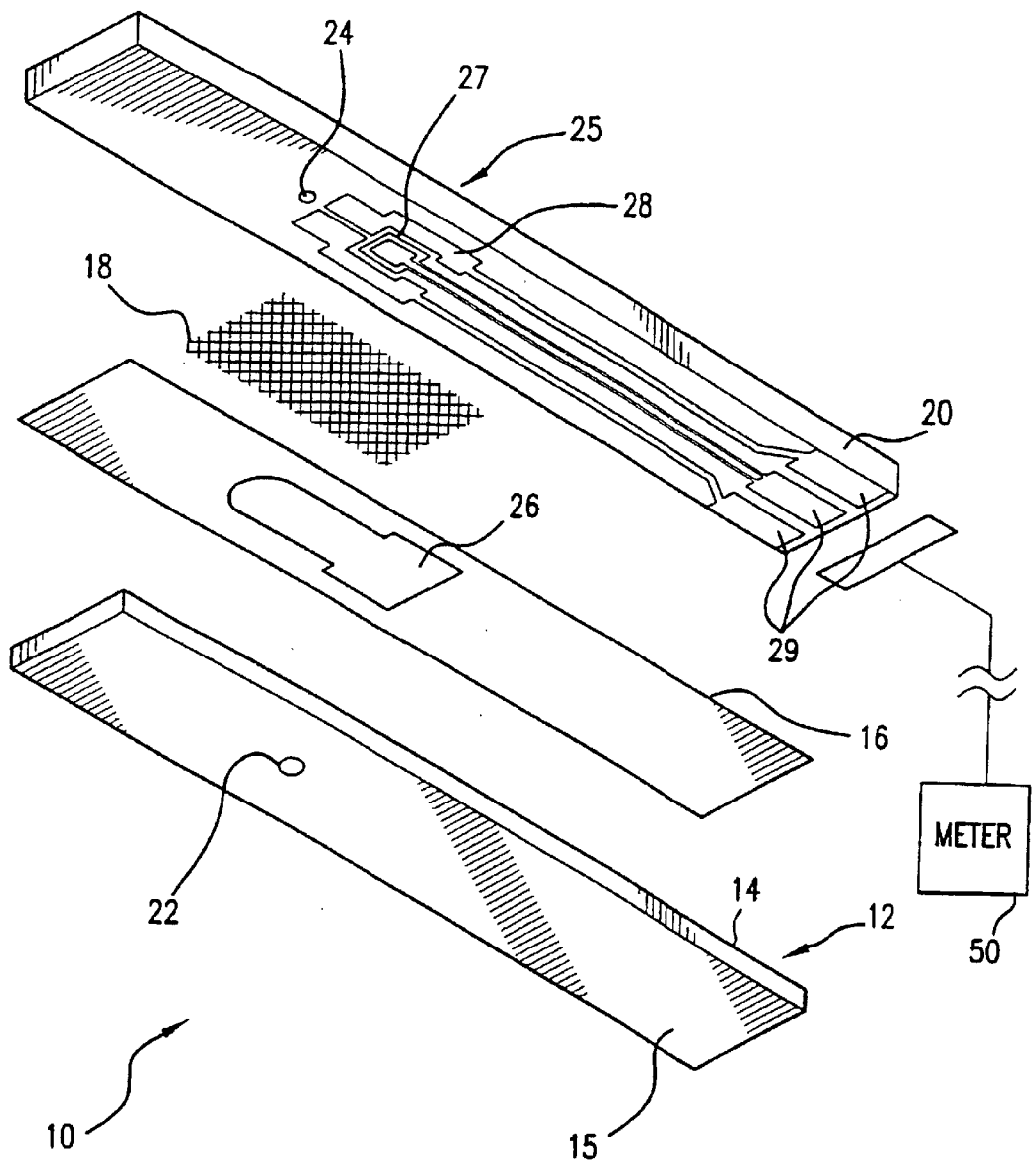
FIG. 1 is an exploded perspective view of an integrated poration, harvesting, and analysis device according to a first embodiment, wherein various layers of the device are depicted in a peeled-apart orientation, with the interior major surfaces of the outermost layers facing each other.

As used herein, the expression "biological fluid" is intended to include blood serum or whole blood as well as interstitial fluid. "Interstitial fluid" is the clear fluid that occupies the space between the cells in the body. The term "stratum corneum" means the outermost layer of the skin, consisting of from about 15 to about 20 layers of cells in various stages of drying out. The stratum corneum provides a barrier to the loss of water from inside the body to the external environment and from attack from the external environment to the interior of the body. The term "epidermis" means the metabolically active region of the skin. It is found just below the stratum corneum and is approximately 10 times as thick as the stratum corneum. The epidermis does not contain blood. The term "dermis" means the region of skin approximately 10 times as thick as the epidermis and found just below the epidermis. The dermis contains large amounts of collagen, which provides structural integrity to the skin. The dermis contains a layer of small blood capillaries that provide oxygen and nutrients to the rest of the layers of skin.

As used herein, the term "tissue" means an aggregate of cells of a particular kind, together with their intercellular substance, that form a structural material. At least one surface of the tissue must be accessible to electromagnetic radiation so that one embodiment of the invention can be carried out. The preferred tissue is the skin. Other tissues suitable for use with this invention include mucosal tissue and soft organs.

As used herein, "sonic energy" refers to mechanical pressure waves with frequencies from 10 Hz to 1000 MHz.

As used herein, "ablation" refers to the process of controlled removing a selected area of tissue from the surrounding tissue by kinetic energy released when vaporizable substances in the selected area is elevated above the vaporization point of water and other vaporizable substances thereby removing some of the tissue in the selected area.

As used herein, "poration," "microporation," or any such similar term means the formation of a small hole or pore to a desired depth in or through a biological membrane, such as skin or mucous membrane, or the outer layer of an organism to lessen the barrier properties of this biological membrane to the passage of biological fluids, such as analytes from within the biological membrane or the passage of permeants or drugs from without the biological membrane into the body for selected purposes, or for certain medical or surgical procedures.

As used herein, the expression "photosensitizing material" means a compound or mixture of compounds that absorb electromagnetic radiation. These compounds are commonly referred to as chromophores. In general, photosensitizing materials include, but are not limited to, photothermal materials. Photothermal materials are compounds, or mixtures of compounds, that absorb electromagnetic radiation and radiate thermal energy.

As used herein, the expression "photosensitizing assembly" means a structure comprising at least one layer containing a photosensitizing material. The structure may take the form of a film, sheet, block, membrane, gel, woven fabric, non-woven fabric, or combination of the foregoing.

As used herein, the term "polymer" means a compound containing repeating structural units. The repeating structural units, i. e., monomers, include, but are not limited to, cellulosics, alkylene, ester, carbonate, amide, acrylic, agar, vinyl, and the like. As used herein, the term "adhesive" means a compound, or mixture of compounds, that promote adhesion between two surfaces.

As used herein, the term "integrated device" means a device suitable for microporating (when coupled to a suitable energy source) at tissue, collecting a biological fluid from the tissue (preferably through the micropores so created) and analyzing the biological fluid to determine a characteristic thereof.

The term "heated probe" means a probe, preferably solid phase, which is capable of being heated in response to the application of electrical or electromagnetic (optical) energy thereto. For simplicity, the probe is referred to as a "heated probe" which includes a probe in a heated or unheated state, but which is heatable.

THE INTEGRATED DEVICE

Figure 9:
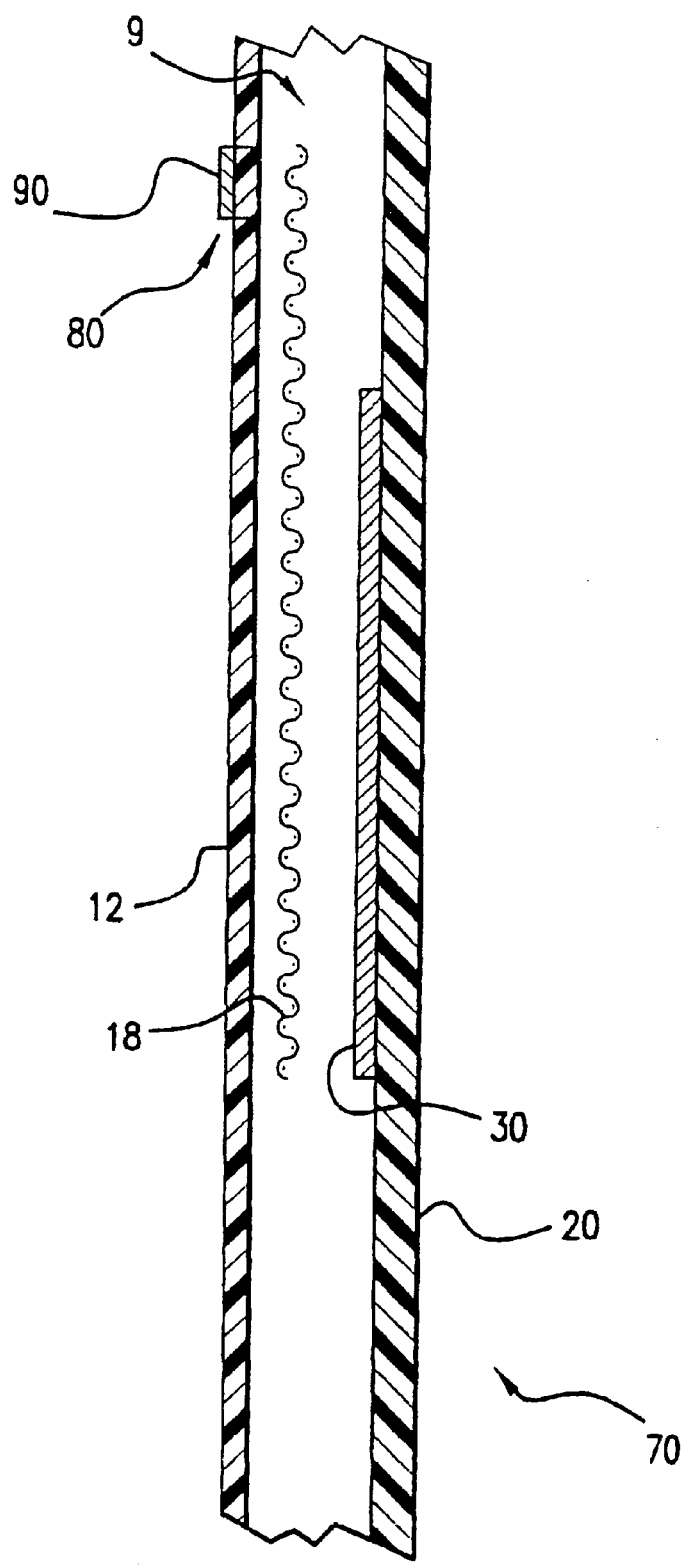
FIG. 9 is an enlarged longitudinal cross-sectional view of an integrated device according to yet another embodiment.
Figure 10:
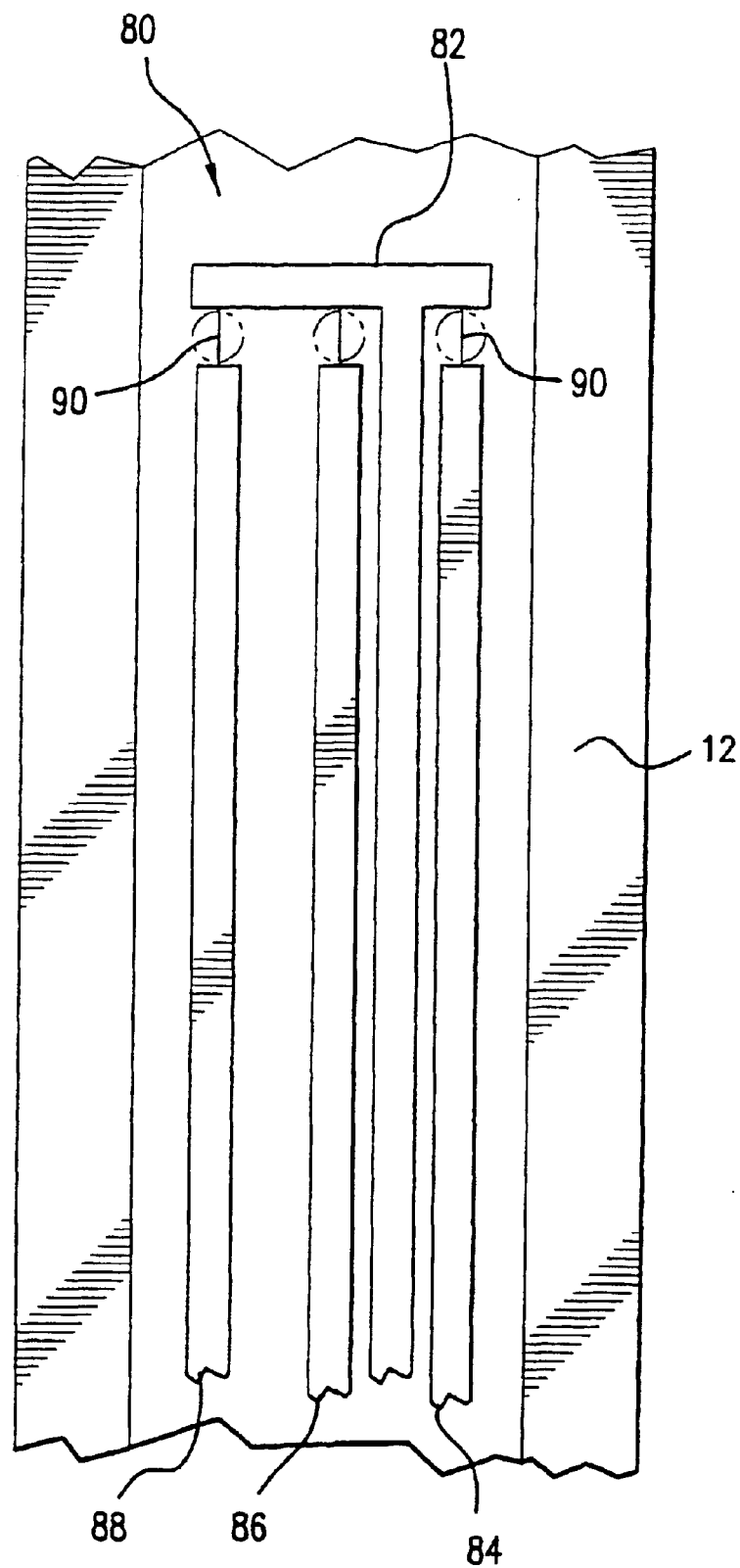
FIG. 10 is a bottom view of a portion of the device shown in FIG. 9, and particularly illustrating the conductors coupled to electrically heatable poration elements.

Several embodiments of the integrated device are disclosed herein. In each of the embodiments, a heated probe or element is provided which, when heated, forms at least one opening, i.e., a micropore, in the tissue. In the embodiments of FIGS. 1–8, the heated probe comprises a photosensitizing assembly which is responsive to optical energy so as to heat up and conduct heat to the tissue. In the embodiment of FIGS. 9 and 10, the heated probe comprises at least one electrically heated probe. What is common among these embodiments is that the heated probe is heated, electrically or optically, such that the temperature of tissue-bound water and other vaporizable substances in a selected area of the surface of the tissue, such as the stratum corneum, is elevated above the vaporization point of water and other vaporizable substances thereby removing the surface of the tissue in the selected area. Consequently, the heated probe forms a micropore in the surface of the tissue approximate 1–1000 $\mu$m in diameter. The integrated device described hereinafter is preferably disposable after a single use.

Some of the microporation techniques described herein are further described in co-pending U.S. application Ser. No. 08/776,863, filed Feb. 7, 1997, entitled "Microporation of Human Skin for Drug Delivery and Monitoring Applications," the entirety of which is incorporated herein by reference.

Integrated Device with Optically Heated Element

Figure 2:
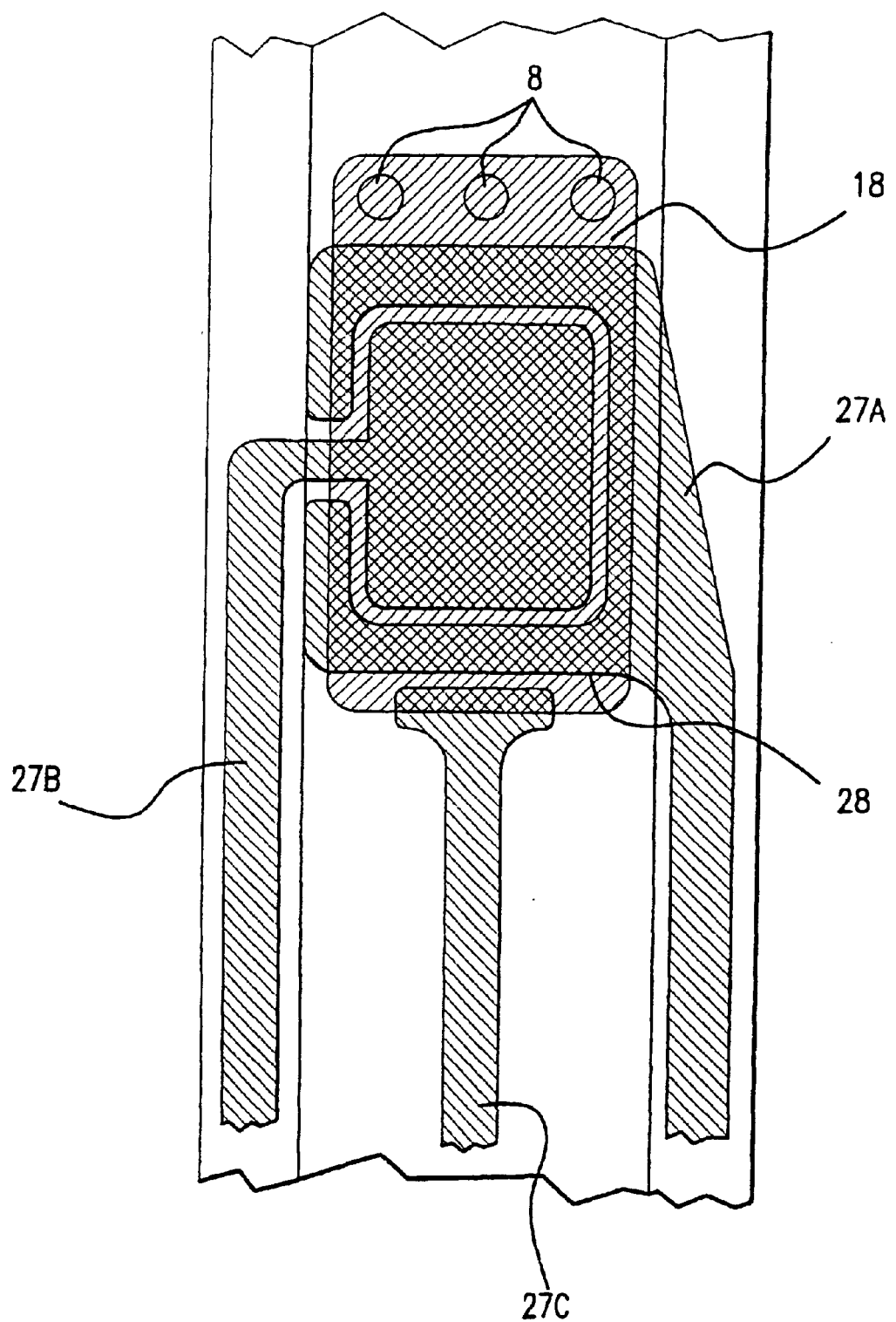
FIG. 2 is a top view of a portion of the device shown in FIG. 1, and particularly illustrating an electrochemical biosensor.
Figure 3:
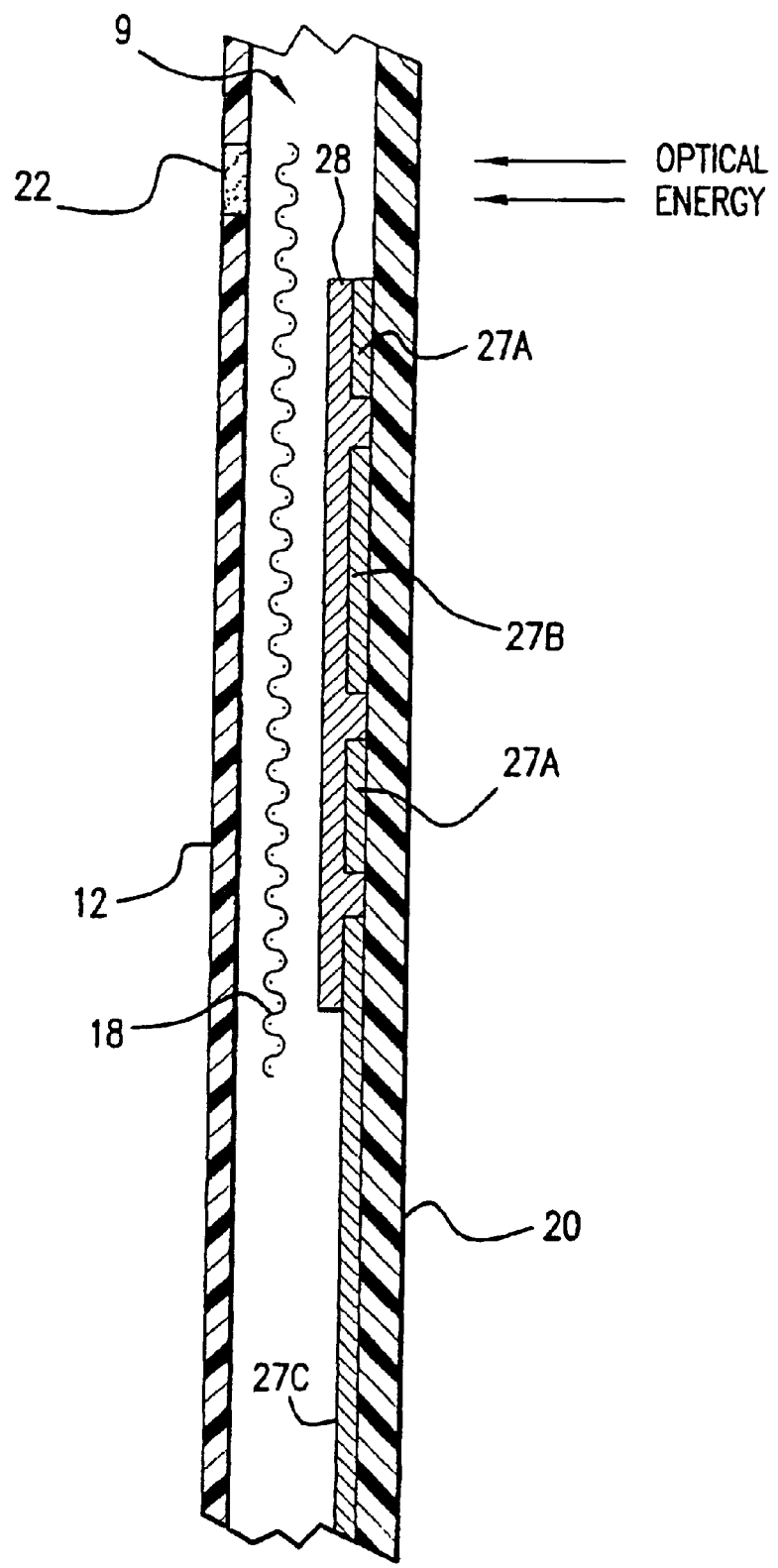
FIG. 3 is an enlarged longitudinal cross-sectional view of the device shown in FIG. 1.

FIGS. 1–3 illustrate a device for integrated device according to one embodiment of this invention. The device 10 comprises a tissue-contacting layer 12, which is designed to be placed in contact with tissue, such as skin, mucosal tissue, etc. An overcoat layer 16 overlies one major surface 14 of tissue-contacting layer 12. The other major surface 15 of the tissue-contacting layer 12 is the surface that actually comes in face-to-face contact with the tissue. Co-planar with the overcoat layer 16 is an optional fluid-transporting layer 18 which is capable of transporting biological fluid, such as interstitial fluid by means of chemically aided wicking. A meter-interface layer 20 overlies the fluid-transporting layer 18. The meter-interface layer 20 has an opening 24 formed therethrough. Alternatively, the entirety or a sufficient portion of the meter-interface layer 20 is made of material transparent to electromagnetic energy at wavelengths used to heat the target element. The overcoat layer 16 is optional, as will become apparent hereinafter, and shown in the cross-sectional view of FIG. 2.

Tissue-contacting layer 12 has a target portion 22 thereon. The target portion 22 and the opening 24 (or the otherwise transparent portion) of the meter-interface layer 20 are aligned so that electromagnetic (optical) energy can pass through the opening 24 and strike the target portion 22. The target portion 22 comprises a photosensitizing assembly and the tissue-contacting layer 12 serves as the substrate for the photosensitizing assembly. The target portion 22 is exposed on both the major surface 14 and on the major surface 15 of the tissue-contacting layer 12. The fluid-transporting layer 18 is also designed to allow the electromagnetic energy, such as optical energy, to pass through it.

The meter-interface layer 20 supports a detecting layer 25 suitable for facilitating measurement of a characteristic of the collected biological fluid, such as glucose concentration. At least a predetermined surface portion of the detecting layer 25 and a predetermined surface portion of the fluid-transporting layer 18 are in fluid communication with each other. While FIG. 2 shows space between these layers for illustrative purposes, it should be understood that in the actual device, the spacing between the layers, if any, maintains fluid communication between the fluid-transporting layer 18 and the detecting layer 25.

In the embodiment of FIGS. 1–3, the detecting layer 25 is an electrochemical biosensor 28 comprised of a layer or layers of chemicals capable of reacting with an analyte in a collected biological fluid to produce a measurable electrical response. U.S. Pat. Nos. 4,545,382 and 4,711,245 describe detecting layers capable of generating a measurable electrical signal in response to glucose in blood.

The electrochemical biosensor 28 is supported on either the tissue-contacting layer 12 or on the meter-interface layer 20. The electrochemical biosensor is flexible so as to conform to the tissue-contacting layer 12, and is transparent or non-transparent. Detecting layers of the electrochemical type preferably comprise a member selected from the group consisting of carbon, silver, platinum, gold, palladium, and silver chloride. Electrodes 27 embedded in the electrochemical biosensor 28 are connected to electrical contacts 29 on the meter-interface layer 20. The meter 50 connects to the electrical contacts 29.

More specifically, as shown in FIG. 2, there are two assay electrodes 27A and 27B which are embedded or otherwise in contact with the sensor area of the electrochemical biosensor 28. Electrodes 27A and 27B are connected to appropriate the electrical contacts 29. In addition, an optional sense electrode 27C is provided at a particular portion of the sensor area of the electrochemical biosensor 28 to detect when the sensor area is sufficiently wetted with the biological fluid to signal an assay reading control system that the assay can be read. European Patent No. 732, 406 discloses an electrode sensor arrangement of FIG. 2.

The meter-interface layer 20 electrically couples the electrochemical biosensor 28 to a meter shown at reference numeral 50 in FIG. 1. Meters suitable for measuring a characteristic of the biological fluid, such as glucose concentration, are well known in the art.

As shown in FIG. 3, the device 10 supports the direct assay for a selected analyte in a biological fluid, which is accessed and harvested via the combination of microporation of the skin, and the placement of the biological fluid sample into the active reagent portion (the electrochemical biosensor 28).

The device 10 comprises a fluid management chamber 9 which functions to direct the biological fluid which exits the body through the pore(s) formed at the poration site(s) 8 onto the electrochemical biosensor 28, as shown in FIG. 2. The micropore(s) are formed at site(s) 8 when the incident optical energy is brought into focus on the target portion 22 coincident with the site(s) 8, heating the photosensitizing-treated film sufficiently to produce both the thermal microporation of the skin contacting it, and also melting to form an opening(s) in the film itself to allow the introduction of the biological fluid through hole(s) created at the target portion. These holes in the tissue-contacting layer are referred to hereinafter as the "inlet ports" of the integrated device.

As shown in FIG. 3, the fluid management chamber 9 is designed to direct the biological fluid towards an active region of the detecting layer 25. This fluid management function may optionally be enhanced by the use of the fluid-transporting layer 18. The fluid-transporting layer 18 and or other surfaces of layers in the fluid management chamber 9 may be selectively treated with chemical substances, such as a wicking agent, or a surfactant to induce the migration of fluid in a particular direction, i.e., to the detecting layer. Alternatively, certain portions of the surfaces of the layers in the fluid management chamber 9, such as the tissue-contacting layer, may be treated with a hydrophobic compounds or substances to direct the biological fluid away from a selected region or regions where it is not desired for the biological fluid to migrate and to direct the biological fluid toward the detecting layer 28. These substances are described in greater detail hereinafter.

The optional sense electrode 27C detects when the biological fluid has wetted the sensor area of the electrochemical biosensor 28. Alternatively, the assay electrodes 27A and 27B themselves can be used to detect when a sufficient volume of biological fluid is present. Once the electrochemical biosensor has been sufficiently wetted, the meter 50 begins the process of reading the biosensor via the assay electrodes 27A and 27B. The electrical properties of the electrochemical biosensor varies in a predetermined manner with the concentration of the selected analyte in the biological fluid. These electrical properties may be any one or combination of a current output, a voltage output, a change in impedance, a change in the time varying profile of the current, voltage or impedance.

The target portion 22 is described in greater detail hereinafter, under the heading "The Target Portion." Briefly, the target portion of the tissue-contacting layer 12 is capable of absorbing electromagnetic energy from a source, such as a laser or other optical source, to heat up and transfer the heat to the stratum corneum, forming a micropore in the skin, at a controlled and desired depth.

The overcoat layer 16 is preferably formed from a polymeric material. Representative examples of polymeric materials suitable for preparing the overcoat layer 16 include polymers formed from acrylic monomers, methacrylic monomers, acrylate monomers, methacrylate monomers, and combinations thereof. The overcoat layer 16 is adhered to the tissue-contacting layer preferably by means of lamination or screen printing.

The fluid-transporting layer 18 transports biological fluid, such as interstitial fluid by means of a wicking action, which may be chemically enhanced. As used herein, the expression "chemically aided wicking action" means the flow of fluid along a material while being aided by at least one chemical substance that is present on the surface of that material. The purpose of the at least one chemical substance is to promote the flow of fluid along the surface of the material. Chemical substances suitable for the surface of the interstitial fluid transporting layer belong to the class of compounds commonly referred to as surfactants. Surfactants reduce the surface tension of the liquid which comes into contact with the surfactant bearing surface. A commercially available surfactant suitable for use in this invention is a fluorochemical surfactant having the trade designation "FC 170C FLUORAD", available from Minnesota Mining and Manufacturing Company, St. Paul, Minn.

The fluid-transporting layer 18 is preferably made from polymeric material. Representative examples of polymeric material suitable for this invention include, but are not limited to, polymers formed from amide monomers, e. g., nylon, ester monomers, alkylene monomers, e. g., polypropylene, polyethylene, cellulosic monomers, and combinations thereof. The amount of surfactant is not critical but it is preferred that the amount of surfactant range from 1 to 10 $\mu$g surfactant per mg of material in the fluid-transporting layer 18. The fluid-transporting layer 18 is capable of allowing electromagnetic energy, such as light from a source, to pass through it. For example, the fluid-transporting layer 18 can be a mesh, whereby the light travels between the strands of the mesh.

Alternatively, the fluid-transporting layer can have a small hole in it, whereby the light passes through that hole. The fluid-transporting layer 18 is capable of allowing an amount of interstitial fluid to uniformly flow through it at a rate such that a sufficient amount of fluid reaches the detecting layer 25 before evaporation causes the amount of the sample to be inadequate to provide an accurate reading of the glucose level.

The meter-interface layer 20 is preferably made from a polymeric material. Representative examples of polymeric material suitable for preparing the meter-interface layer 20 include polymers formed from acrylic monomers, methacrylic monomers, acrylate monomers, methacrylate monomers, vinyl chloride monomers, and combinations of the foregoing. Other polymers suitable for preparing the meter-interface layer 20 include polyesters. The overcoat layer 16 is adhered to the meter-interface layer 20 preferably by means of lamination or screen printing. The functions of the meter-interface layer 20 are to (1) provide a surface on which to print or dispose the detecting layer 25, (2) provide alignment of the laser target on the multiple-layer article with the energy source, (3) provide contact points on the device so that the meter can read the signal from the detecting portion of the device, and (4) provide a support layer so that the device can be easily handled and placed in contact with the meter.

The following table lists suitable ranges for the dimensions of the layers of the device. It is not intended that the dimensions of the layers be limited to the ranges listed in the table.

| Layer | Major surface dimension (mm) | Minor surface dimension (mm) | Thickness (mm) |
| --- | --- | --- | --- |
| Skin-contacting | 60 to 5 | 5 to 60 | 0.05 to 2.0 |
| Overcoat | 60 to 5 | 5 to 60 | 0.05 to 0.5 |
| Fluid transporting | 60 to 5 | 5 to 60 | 0.05 to 0.5 |
| Detecting | 60 to 5 | 5 to 60 | 0.01 to 0.5 |
| Meter contacting | 60 to 5 | 5 to 60 | 0.05 to 2.0 |

The device 10 is preferably sufficiently flexible so that it can conform to the shape of a body part, and sufficiently rigid so that it can be easily handled by the user. In preferred embodiments, at least one of the tissue-contacting layer 12 and the meter-interface layer 20 is made of a material that is sufficiently flexible to conform to the shape of a body part, but is still sufficiently rigid to support the overcoat layer 16, the fluid-transporting layer 18, and the detecting layer 25.

The porosity of the layers of the device 10 is dependent upon the positioning and functionality of the layer. The tissue-contacting layer 12, the overcoat layer 16, and the meter-interface layer 20 should be sufficiently non-porous to form a well or chamber for the interstitial fluid. The fluid-transporting layer 18 should be sufficiently porous to allow interstitial fluid to flow uniformly and rapidly therethrough to the detecting layer 25. The porosity of the detecting layer 25 is not critical; it can be porous or non-porous depending upon the design selected by the manufacturer.

The surface dimensions of the overcoat layer 16 are preferably identical to that of the tissue-contacting layer 12. The opacity of the overcoat layer is not critical so long as there is an unobstructed path to the target portion 22 on the tissue-contacting layer 12.

The surface dimensions of the overcoat layer 16 are preferably less than those of the meter-interface layer 20 so that the electrical contacts 29 are exposed to facilitate insertion into a meter. The opacity of the fluid-transporting layer 18 is not critical unless it overlaps the path between the target portion 22 and the opening 24, in which case, it should be transparent to the electromagnetic radiation.

The surface dimensions of the meter-interface layer 20 are preferably larger than those of the tissue-contacting layer 12 so that electrical contacts 29, in the case of electrochemical sensors, are easily accessible for insertion into the meter 50.

Referring to FIGS. 4 and 5, in the form of the device 10 that includes the overcoat layer 16, the overcoat layer 16 and the fluid-transporting layer 18 are preferably substantially co-planar in the assembled device 10. Substantial co-planar positioning of these layers is preferred because the fluid-transporting layer 18 spreads fluids in all directions. In order to limit the spread of fluid to undesired areas, the overcoat layer 16 acts as a barrier to flowing fluid. The fluid-transporting layer 18 is adhered to the tissue-contacting layer 12 by means of embedding the edges of the fluid-transporting layer 18 into the overcoat layer 16. As used herein, the expression "substantially co-planar" includes both the situation wherein at least one major surface of the overcoat layer 16 and at least one major surface of the fluid-transporting layer 18 are in the same plane and the situation wherein at least one major surface of the overcoat layer 16 extends slightly beyond at least one major surface of the fluid-transporting layer 18. Perfect co-planarity, i.e., the former situation, is difficult to achieve primarily because of manufacturing conditions. Substantial co-planarity, i.e., the latter situation, is more likely to be achieved under actual manufacturing conditions, and is shown in FIGS. 4 and 5. However, it is preferred that the overcoat layer 16 and the fluid-transporting layer 18 approach perfect co-planarity as much as possible so that the volume of interstitial fluid required for analysis is as small as possible.

Figure 6:
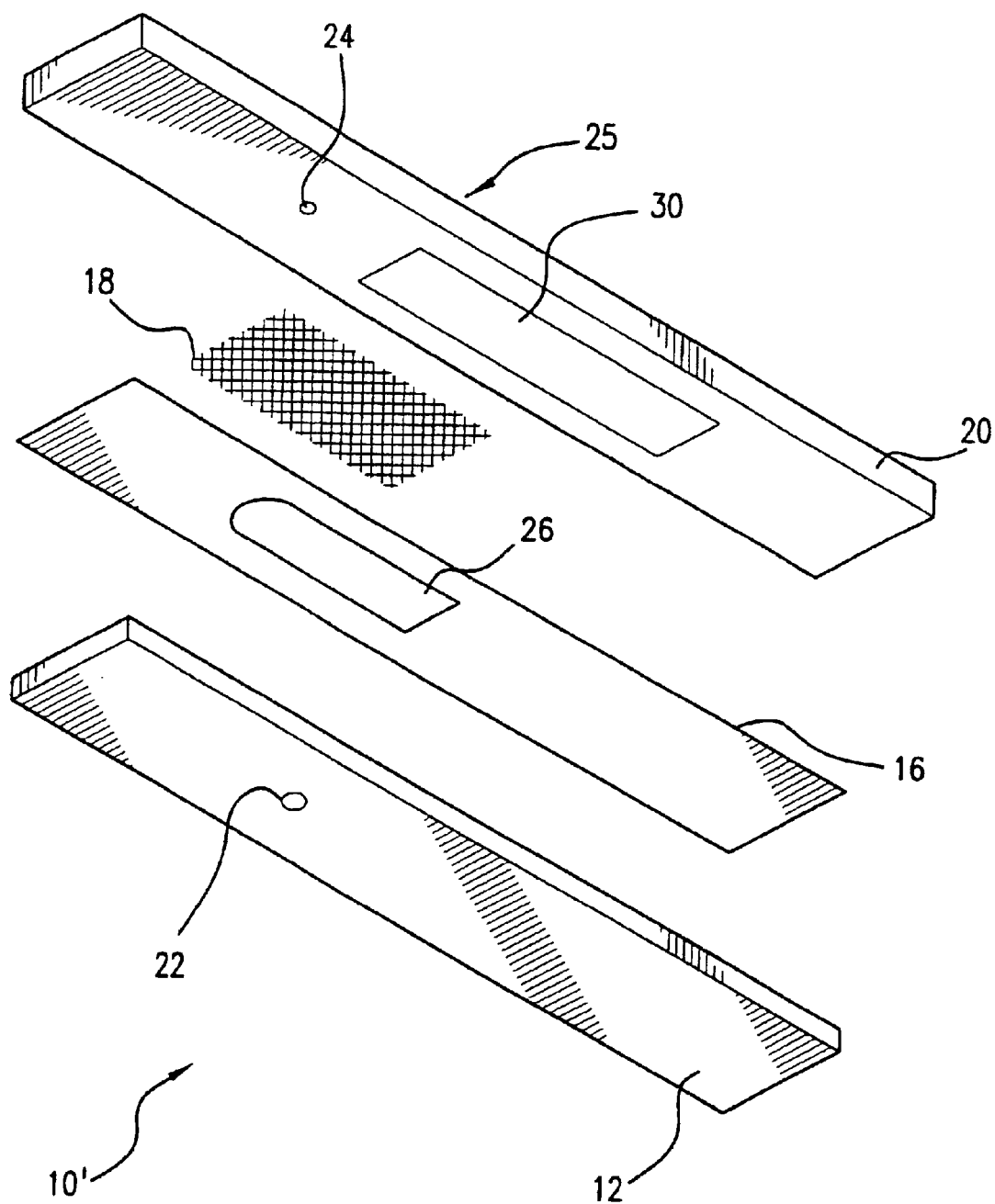
FIG. 6 is an exploded view, similar to that of FIG. 1, of an integrated device according to another embodiment.
Figure 7:
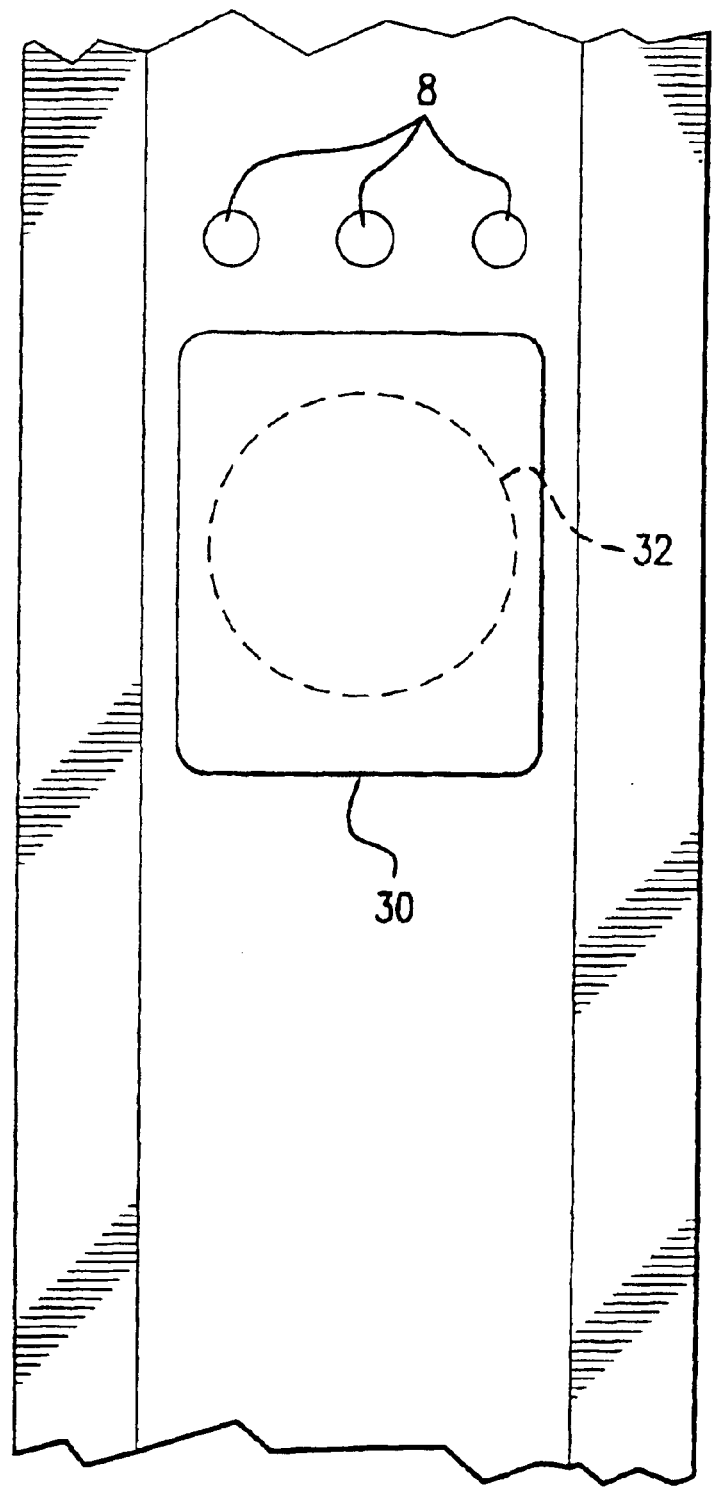
FIG. 7 is a top view of a portion of the device of FIG. 6, and particularly showing the calorimetric sensor.
Figure 8:
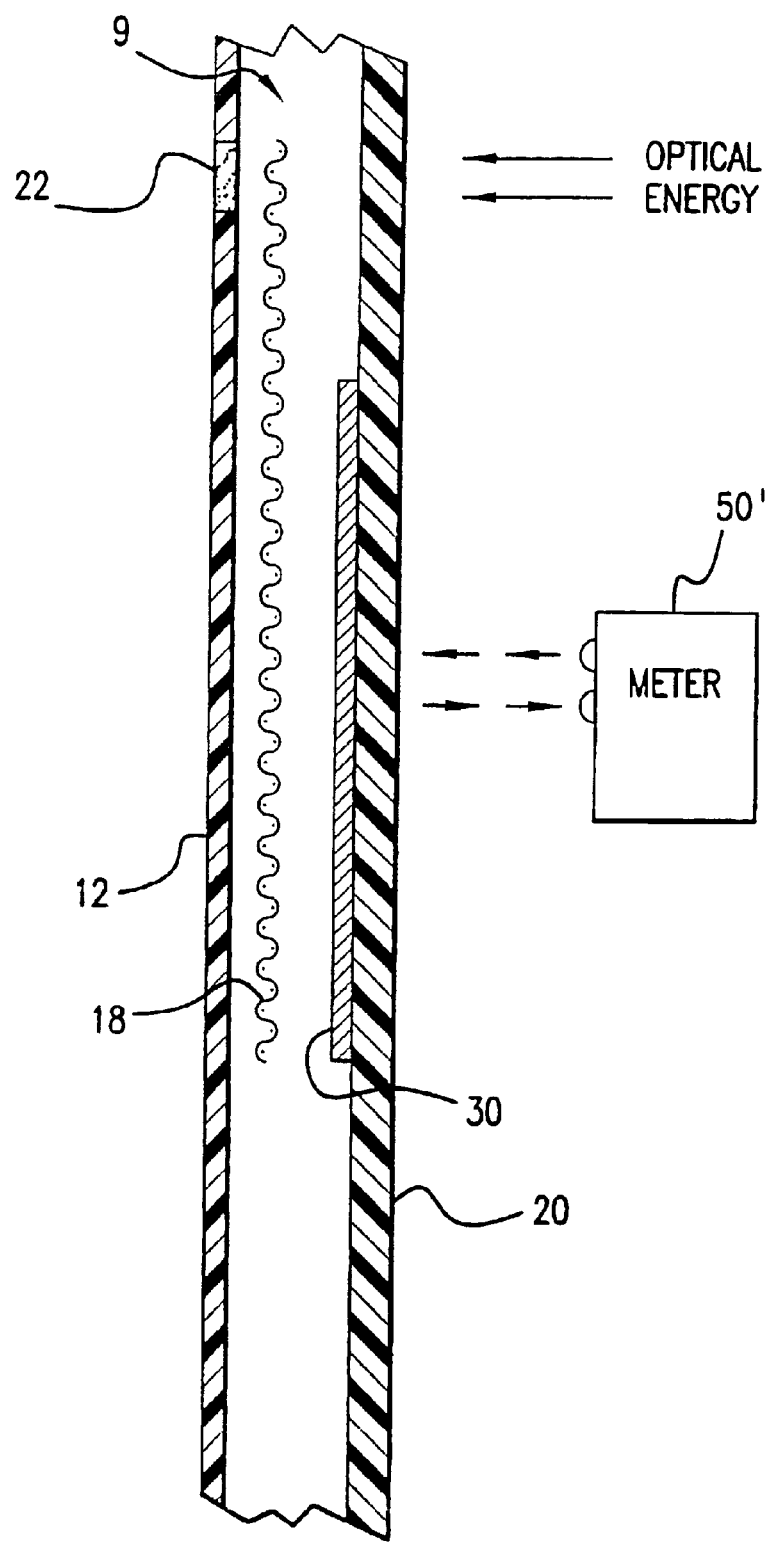
FIG. 8 is an enlarged longitudinal cross-sectional view of the device shown in FIG. 6.

In another embodiment of the device, shown at reference numeral 10' in FIGS. 6–8, the detecting layer 25 includes a photometric sensor, such as a calorimetric sensor, shown at reference numeral 30. U.S. Pat. Nos. 4,935,346 and 4,929,545 disclose suitable detecting layers capable of producing a measurable change in optical reflectance in response to glucose in biological fluid, hereinafter called a colorimetric sensor. The colorimetric sensor 30 is preferably porous, and contains the reagents required to cause a chemical reaction that is used to provide an indication of the concentration or presence of analyte in the collected fluid. In the case of glucose monitoring, these reagents include, but are not limited to, glucose oxidase, glucose dehydrogenase, and peroxidases. The colorimetric sensor 30 comprises at least one dye and at least one enzyme. Other examples of photometric sensors are well known in the art, some of which are described hereinafter.

The device 10' is the same in most other respects to the device 10 shown in FIGS. 1–5. However, as shown in FIG. 8, in the device 10', the meter-interface layer 20 is transparent in a region of the meter-interface layer 20 aligned with the calorimetric sensor 30 so as to permit a meter 50' to transmit light to the colorimetric sensor 30 and detect the reflectance of light therefrom. The amount of light reflected from the colorimetric sensor 30 is indicative of the concentration of glucose in the collected fluid. Examples of suitable meters 50' which are used to measure glucose concentration using a standard reflectance measurement at the appropriate optical wavelengths to quantify the amount of the selected analyte present in the sample are well known in the art As shown in FIGS. 7 and 8, the colorimetric sensor element 30 is positioned on the underside of the optically transparent meter-interface layer to allow the color detection system to access the back side of this region. The look field of the meter 50', shown as a circle in phantom at reference numeral 32, is shown to define the desired total fluid volume needed to fill the fluid management chamber 9. The optional fluid-transporting layer 18 may be used to help manage and distribute the fluid in a manner similar to that described in the previous embodiment of FIGS. 1–3.

The location of the micropore(s) 8 may be placed with less accuracy in this design because there are no electrode paths. For example, the target portion 22, and thus the formation of the micropore(s) 8 can be directly under the colorimetric sensor 30, by placing holes in it, and then compensating for any loss of signal during the optical measurement of the color shift. Moreover, when the target portion 22 is heated by electromagnetic energy, portions of it melt away in the course of heating and conducting the heat to the tissue, thereby forming inlet ports into the fluid management chamber 9 of the integrated device 10 and 10'.

As shown in FIG. 6, alternatively, if the optional overcoat layer 16 is included, it is provided with an aperture 26 formed therein to expose the fluid-transporting layer 18 so that interstitial fluid from a micropore created in the stratum corneum contacts the fluid-transporting layer 18.

In the device 10', the colorimetric sensor 30 is held in very precise registration to enable the optical field of view of the optical meter to be precisely placed in the center of the region of the calorimetric sensor 30 wetted by biological fluid. This reduces the actual volume of biological fluid required to produce an accurate reading of the amount of the selected analyte present in the biological fluid.

Specifically, it is a standard concept in the design of disposable assay strips to completely wet an area of the reagent treated portion of the assay strip much larger, typically 5 to 10 times larger, than the total area actually read by the meter. This practice allows relaxation of manufacturing tolerances in many parts of the system. This is also a common feature in the "fingerstick" blood-based glucose monitoring systems due to the physical difficulty of the user placing a smaller sample only on the actual target spot as well as the need for most whole blood-based systems to separate the corpuscular components from the serum. By incorporating the automatic registration of the micropores 8 with the biosensor through the design of the device, the assay process can be conducted accurately with a much smaller sample of the fluid than the typical fluid based disposable assay technology currently available.

The assay technique used in connection with the device 10' may be based on a fluorescent intensity technology. In this case, the colorimetric sensor is treated with a probe fluorophore. A reaction between a probe fluorophore and the selected analyte produces a predictable change in the fluorescent intensity of the probe molecules when excited with a particular optical wavelength such that the subsequent fluorescence is detected at a selected longer wavelength. Optionally, the fluorescent probe is selected such that it can emit in two different wavelength bands, wherein the intensity of energy in only one of the bands is predictably modified by the varying concentration of the selected analyte. A ratiometric processing of the two different fluorescent intensities can be employed, thereby simplifying the calibration of the reading and allows for self-adjustment for different amounts or areas of the calorimetric sensor 30 wetted with the biological fluid. Moreover, the fluorescent interrogation field of view may be defined by the intersection of the incident excitation light and the look field of the fluorescent receive channels.

Further still, the assay technique used in conjunction with the device 10' may be based on a fluorescent lifetime based assay technology. In this case, a reaction between a probe fluorophore, with which the colorimetric sensor 30 is treated, and the selected analyte produces a predictable change in the fluorescent lifetime of the probe molecules when excited with a particular wavelength. The subsequent fluorescent lifetime is detected at a selected longer wavelength. The detection of the fluorescent lifetime may be accomplished by either measuring directly the decay of the fluorescence in response to a known pulse shape of excitation light, or by measuring the phase shift and modulation depth of the fluorescent signal in response to the excitation of the sensor by a periodic modulated light source at the appropriate excitation wavelength. By basing the quantification of the analyte on a time resolved measurement, much of the difficulty associated with the calibration of an absolute intensity based measurement is overcome. Also, the signal-to-noise aspects of such a system are easily optimized. For example, in a phase detection system, it is routine to integrate for a sufficient period of time in order to resolve the phase to any level needed. Consequently, very small amounts of the probe molecule and biological fluid may be utilized to achieve the desired level of quantification of the selected analyte, yielding additional benefits in the potential reduction of the required biological fluid sample volumes to the levels of only a few hundred nanoliters.

The Target Portion

The target portion 22 consists of a photosensitizing assembly which includes a photosensitizing material provided in such a manner that it can be applied to tissue in a reproducible manner. This ensures that the quantity of photosensitizing material to which the tissue is exposed can be known accurately.

Photosensitizing materials suitable for use in this invention are capable of absorbing electromagnetic radiation at one or more wavelengths. Electromagnetic radiation considered to be suitable for this invention include radiation from the ultraviolet, visible and infrared regions of the electromagnetic spectrum. It is preferred, however, that visible radiation and infrared radiation be employed. Ultraviolet radiation has a wavelength ranging from about 10 nm to about 380 nm. Visible radiation has a wavelength ranging from about 380 nm to about 780 nm. Infrared radiation has a wavelength ranging from about 780 nm to about 50,000 nm. Photosensitizing materials suitable for use in this invention include, but are not limited to, dyes and pigments. The term "pigment" is used to describe the class of colorants that are practically insoluble in the media in which they are applied. Pigments retain a particulate form, suspended in the media. The term "dye" is used to describe colorants that are soluble, or at least partially soluble, in the media in which they are applied. Dyes exhibit an affinity to the substrate to which they are applied. Classes of dyes that are suitable for use in this invention include, but are not limited to, diphenylmethane dyes, methin-polymethine dyes, porphine dyes, indathrene dyes, quinones, dithiol metal complexes, dioxazines, dithiazines, polymeric chromophores. Classes of pigments that are suitable for use in this invention include, but are not limited to, carbon black, carbon based pigments, metals, metal sols, dyed latexes, and inorganic pigments. Colorants that are preferred for this invention include copper phthalocyanine, indocyanine green, nigrosin, prussian blue, colloidal silver (20 to 100 nm diameter), carbon black, IR-780, IR-140, irgalan black, naphthol green B, tellurapyryllium, and vanadyl tetra-t-butyl-naphthalocyanine. In either case, particles of the dyes or pigments must be of a size that they can readily be blended with carrier materials. Carrier materials suitable for use with dyes and pigments include, but are not limited to, solid polymers, adhesives, gels, liquids, glass and paper. These materials comprise polymeric materials such as acrylics, silicones, polyesters, polycarbonates, polyimides, cellulosics, polyvinyl derivatives, polyethylene, polypropylene, and the like. It is preferred that the particles of dyes and pigments have a major dimension, e. g., length, diameter, no greater than about 50 $\mu$m and preferably less than 5 $\mu$m.

The photosensitizing material preferably does not melt or decompose at temperatures below about 120° C., and is capable of absorbing an amount of electromagnetic energy and converting it to an amount of thermal energy sufficient to cause ablation of the tissue by the mechanism of conduction.

In one embodiment of this invention, the photosensitizing material is applied to the tissue-contacting layer 12 to form the target portion by means of a carrier. The tissue-contacting layer 12 serves as a substrate. The carrier is a material in which the photosensitizing material can be uniformly dissolved if the photosensitizing material is a dye, or uniformly suspended if the photosensitizing material is a pigment. Carriers that are suitable for dyes or pigments include, but are not limited to, solid polymers, adhesives, gels, and oils and greases.

The concentration of photosensitizing material in the carrier can vary. A sufficient concentration of dye is typically that required to obtain an optical density greater than 1.0 at the wavelength of the laser. Determination of the appropriate concentration can readily be determined by trial-and-error by one of ordinary skill in the art.

In addition to the photosensitizing material, other ingredients that can be added to the carrier, but are not limited to, plasticizers, surfactants, binders, and crosslinking agents. These materials are commercially available.

In general, substrates to which the carrier containing the photosensitizing material can be applied (i.e., the tissue-contacting layer) include, but are not limited to, polymeric materials, cloth, non-woven materials, microporous membranes, glass, and metal foils. The substrate is preferably sufficiently flexible to allow close contact with the tissue. The substrate should adhere sufficiently to the carrier so that it does not detach before or during use. Materials that are suitable for preparing the substrate include, but are not limited to, polyesters, polyimides, polyethylenes, polypropylenes, polycarbonates, acrylics, cellulose, derivatives of cellulose, and the like.

In another embodiment, the photosensitizing material is blended with a film-forming material which forms the tissue-contacting layer. The film-forming material is preferably capable of being formed into a film that will allow uniform suspension of the photosensitizing material and will allow sufficient flexibility to conform to the tissue of the subject. Film-forming materials suitable for use in this embodiment include, but are not limited to, polyesters, polyimides, polyethylenes, polypropylenes, polycarbonates, acrylics, cellulose, derivatives of cellulose, and the like. Other substances can be combined into the suspension with the photosensitizing material, such as flux enhancer compounds that can be vaporized when the photosensitizing assembly is heated, thereby being released into microporated tissue for acting on the tissue.

The thickness of the tissue-contacting layer is not critical, but preferably ranges from about 0.05 mm to about 2.0 mm. The surface dimensions of this layer are not critical, but the major dimension preferably ranges from about 5 mm to about 60 mm and the minor dimension preferably ranges from about 5 mm to about 60 mm. The tissue-contacting layer 12 is shown as being rectangular, but other shapes are also suitable, e. g., circular, elliptical, triangular, square, and other shapes. The tissue-contacting layer 12 can be adhered to the skin of the subject by means of adhesive, electrostatic force, or pressure applied by the subject. The seal between the skin and the tissue-contacting layer 12 should be sufficiently tight so that biological fluid does not leak through or into it.

There are several ways to prepare the tissue-contacting layer 12 with the target portion 22. According to one method, a pigment, e.g., carbon black, can be suspended uniformly into a pressure-sensitive adhesive composition. The adhesive composition can then be cast, or printed, onto a polymeric substrate. The adhesive composition can then be cured. According to another method, a dye, e.g., copper phthalocyanine, can be suspended in an organic solvent, e.g., ethanol. The suspension can be applied to one side of a polymeric membrane by means of an air-brush. The film can then be allowed to dry. According to still another method, a pigment, e.g., carbon black, can be suspended in a polymer based ink, such as clear nail polish. The ink can then be cast, or printed, onto a polymeric substrate. The film can then be cured. According to yet another method, a pigment, e.g., carbon black, can be blended into a polymeric material, e.g., linear low density polyethylene. The blend can then be melted and extruded into a film. The film can then be cured. Regardless of how the tissue-contacting layer is prepared, the major surface 15 is the surface that is intended to come into contact with the skin.

The photosensitizing assembly has utility in many applications, including, but not limited to, the integrated device disclosed herein. The photosensitizing assembly can be applied to the tissue in a variety of ways. In the case of the photosensitizing assembly mixed with a carrier, the carrier can be a pressure-sensitive adhesive, which adheres the assembly to the tissue. In the case of the film, the film can be adhered to the tissue by means of electrostatic force. Other means of attachment include pressure applied to the film and vacuum to evacuate the area between the film or photosensitizing assembly and the tissue to draw the film into contact with the tissue. Combinations of means of attachment can also be used.

The photosensitizing assembly of the present invention overcomes several problems of the prior art, in particular in the manner of application. Specifically, pastes, or suspensions, of photosensitizing material have been applied topically to the target tissue. These materials have led to non-uniform and uncontrolled exposure to radiation from the laser. Variable and inaccurate application of the photosensitizing material can lead to unreproducible results of the photothermal treatment.

In addition, previous methods of applying a photosensitive dye to tissue give rise to difficulty in removing the excess dye following photothermal treatment. This difficulty also brings about the potential for contamination of adjacent tissue, clothing, etc., with residual dye.

The photosensitizing assembly according to the present invention deploys photosensitizing material in such a manner that it can be readily removed from the tissue and discarded following photothermal treatment. Moreover, the photosensitizing assembly deploys a photosensitizing material with reproducible results.

The following are examples of the photosensitizing assembly.

EXAMPLE 1

Carbon black (20 nm) was suspended uniformly into an acrylic-based, pressure-sensitive adhesive (Aroset A 1081, Ashland Chemical) to provide a suspension having a concentration of 20 g carbon black/liter. The resulting suspension was cast onto a polyester film (25 $\mu$m thick). The adhesive was then cured by heating. After curing, the adhesive layer was approximately 50 $\mu$m thick. The combination of carbon black-adhesive and film substrate constituted the photosensitizing assembly. A 0.4 inch diameter circle of the photosensitizing assembly was prepared and placed on the volar forearm of the subject. Light from a 1 Watt, CW laser diode of 810 nm (Coherent Inc., Santa Clara Calif., part #S-81-100C-100T) was collimated and focused to a spot size of approximately 80 $\mu$m in diameter at the plane of the surface of the skin. At 250 mW peak power at the skin, 30 pulses of 50 msec each were delivered, each with 80 msec delays between pulses. The pulsing sequence was repeated to produce 6 photothermally treated sites spaced on the circumference of a 1.0 mm circle. After removal of the photosensitizing assembly, the presence of the resulting small pores in the stratum corneum could be detected or observed.

EXAMPLE 2

Carbon black (<1$\mu$m) was suspended into an acrylic-based ink, such as clear nail polish, to provide a suspension having a concentration of 10 g/l. The suspension was then cast, or printed, onto a polyester substrate (0.050 mm thick). The suspension was cured. The resulting coated substrate was then applied topically to the skin either directly, as a film, or, indirectly, as part of a device. Light from a laser or from a polychromatic light source was focused onto the film and interface between the colorant and the skin for the photothermal treatment. Following the photothermal treatment, the film was removed and discarded.

EXAMPLE 3

Carbon black (<1 $\mu$m) was blended into polyester to provide a blend having a final concentration of 10 g/l. The blend was commercially available under the trade designation "MELINEX 427/200." The blend was melted, and the melted blend was then extruded to form a film (0.050 mm thick). The film was then cured. The resulting film was then applied topically to the skin, either directly as a film or indirectly as part of a device. Light from a laser or from a polychromatic light source was focused onto the film and interface between the colorant and the skin for the photothermal treatment. Following the photothermal treatment, the film was removed and discarded.

EXAMPLE 4

Titanium metal was sputter-coated onto a polycarbonate film substrate. The substrate has a thickness of 2 mil (0.05 mm). The thickness of the titanium/titanium oxide layer was approximately 50 nm. The film was placed onto the skin, the metal layer being in contact with the skin. The film was maintained in proper position by an adhesive ring, which surrounded the targeted area. Light from a laser or from a polychromatic light source was focused onto the film and interface between the colorant and the skill for the photothermal treatment. Following the photothermal treatment, the film was removed and discarded.

The metal layer can be coated with a thin layer of polymeric material, such as 0.25 mil (0.006 mm) of polyoxymethylmethacrylate, as a protective layer.

EXAMPLE 5

The photosensitizing assembly of Example 1 was placed onto the skin over the area to be treated. Light from a laser was focused onto the assembly to create a small region of thermally treated stratum corneum. The treated region was characterized by loss of adhesion of underlying cells. The region appears as a small pore surrounded by an area of loose skin, or an area resembling a small blister in which the cell adhesion in the epidermal layer has been disrupted. This treatment was repeated such that the individually treated areas overlap. When the adhesive was removed, the treated stratum corneum and some of the epidermis underlying the stratum corneum was removed. Remaining epidermis may be removed by mild abrasion with a sterile cotton swab. The treatment generally does not result in bleeding.

EXAMPLE 6

The method described in Example 5 was performed with an adhesive-free photosensitizing assembly. Following photothermal treatment, the affected tissue was removed by mild rubbing with a cotton swab or by applying a sterile adhesive film, which can remove the tissue with the removal of the tape.

EXAMPLE 7

A small vacuum chamber having an orifice of 9 mm in diameter was placed over the skin, covering the 6 micropores, formed according to the procedures of Example 1. The chamber was evacuated to −6.00 psi for a period of two minutes. After the vacuum was released, the resulting clear fluid was collected by means of a micro-capillary tube. Volumes of 0.25 to 0.75 $\mu$l were routinely obtained through use of this protocol. The presence of fluid indicated that the photothermally generated pores had penetrated the stratum corneum into the underlying epidermis, breaching the barrier properties of the stratum corneum. No measurable fluid was obtained with application of the vacuum to untreated skin.

EXAMPLE 8

Samples of interstitial fluid were obtained as described in Example 7. The clear fluid was diluted into 1.0 ml of 5 mM phosphate, 0.02% sodium azide, pH 7.0. At the same time of sampling the interstitial fluid, blood plasma samples were obtained from the same subject. The finger of the subject was pierced with a lancet device, and blood was collected into a capillary tube containing heparin. The blood sample was centrifuged to separate the plasma fraction from the cellular fraction. A sample of 1.0 $\mu$l of plasma was transferred to 1.0 ml of phosphate buffer diluent by means of a micro capillary tube. The dilute samples of interstitial fluid and plasma were analyzed for glucose content by means of high pressure liquid chromatography with pulsed amperometric detection (HPLC-PAD). HPLC-PAD analysis was performed by using a Dionex PA-1 column, 4.0×250 mm, operated with a flow rate of 1.0 ml/min with 150 mM sodium hydroxide. Injection volumes of 10 $\mu$l were made. Glucose demonstrated a peak retention time of 4.0±0.3 minutes. Samples were compared to known aqueous and serum standards containing glucose, and concentrations were determined from the area of the glucose peak. The results contained from six healthy, non-diabetic subjects are set forth in the following table, where the units of glucose are mg/dl.

| Subject | Glucose in interstitial fluid | Glucose in plasma |
| --- | --- | --- |
| A | 102 | 116 |
| B | 123 | 143 |
| C | 147 | 123 |
| D | 113 | 120 |
| E | 88 | 94 |
| F | 102 | 105 |

EXAMPLE 9

To demonstrate the ability to deliver substances through the stratum corneum, sodium fluorescein was used as a model tracer. The volar forearm of a test subject was treated as in Example 1 to prepare a set of 6 pores comprising a circular pattern approximately 1.1 mm in diameter. Following poration, 1.0 $\mu$l of 10% sodium fluorescein in sterile saline was placed on the skin, covering the pores. A control area of skin, free of formed pores, was similarly covered with 1.0 $\mu$l of sodium fluorescein solution. After two minutes, the excess solution was removed by blotting, followed by washing with mild detergent, rinsing, and blotting dry. Where pores were formed, the skin demonstrated visible pigmentation due to the presence of fluorescein within the tissue. The area of yellow staining was approximately 1.4 mm in diameter. No staining was apparent for the control area. Under ultraviolet illumination, the area of the skin where pores were formed demonstrated intense yellow-green fluorescence covering an area of approximately 1.5 mm in diameter, due to the presence of the sodium fluorescein. The immediate area which outlined each of the six pores was more intensely fluorescent. In addition, there was a light fluorescence covering an area of approximately 2.0 mm in diameter which appeared to be due to some residual fluorescence in the outer stratum corneum.

The photosensitizing assembly can be used to form a pore in the stratum corneum. Generation of small pores in the stratum corneum may be used to gain access to body fluids for diagnostic applications. Additionally, poration may be used to increase the permeability of some drugs or other bioactive agents. The present invention may also be applied in surgical applications such as the treatment of surface lesions, tattoos, or other photothermal treatments of tissue surfaces.

In summary, the photosensitizing assembly, in one embodiment, comprises a quantity of photosensitizing material; a carrier which is combined with the photosensitizing material such that the photosensitizing material is substantially uniformly dissolved or suspended therein; and a substrate to which the carrier-photosensitizing material combination is applied. A layer of priming material may be provided between the substrate and the carrier. In another embodiment, the photosensitizing assembly comprises a quantity of photosensitizing material; and a film material containing a substantially uniform suspension of the photosensitizing material.

Further, a method for treating tissue is provided, which comprises the steps of applying a photosensitizing assembly including a quantity of photosensitizing material to tissue, and subjecting the photosensitizing assembly to electromagnetic radiation. The step of applying may comprise applying a substrate, to which is applied a carrier incorporating a substantially uniform suspension of the photosensitizing material. The substrate may be adhered to the tissue. Alternatively, the step of applying may involve applying a film incorporating a substantially uniform suspension of the photosensitizing material.

Integrated Device with Electrically Heated Probe(s)

In the previous embodiments of the integrated device, the poration process is based on the application of optical energy to an absorber target which in turn heats up sufficiently to conductively deliver enough thermal energy to the skin to ultimately cause the desired thermally induced microporation. An alternative approach to delivering this heat energy to the poration sites involves the placement of an electrically heated probe directly at the poration site. The temperature of the electrically heated probe is modulated as needed to effect the microporation process.

A schematic representation of an integrated device employing an electrically heated probe is shown in FIGS. 9 and 10. The device 70 comprises a tissue-contacting layer 12, an optional fluid-transporting layer 18, a meter-interface layer 20, and a detecting layer, which in this example, is a calorimetric sensor 30. It should be understood, however, that this same concept could easily be modified to employ the electrochemical biosensor 28, shown in FIGS. 1–3. Moreover, as described in the foregoing, many of the aspects of the assay/fluid management systems of the device are optional, such as the use of the fluid-transporting layer 18, surfactant treated portions of the fluid management chamber, optically transparent windows in the layers to allow the reading of a calorimetric assay, etc.

In the device 70, the photosensitizing assembly at the target portion is replaced with at least one electrically heated probe 80. The types of electrically heated probes that are suitable are disclosed in the aforementioned co-pending U.S. application Ser. No. 08/776,863, which is incorporated herein by reference.

As shown in more detail in FIG. 10, the electrically heated probe 80 comprises an electrically conductive element or wire 90 provided on the bottom surface of the tissue-contacting layer 12. Three electrically conductive elements 90 are shown as an example, though any number of them may be provided. An electrical conductor 82 extends the length of the tissue-contacting layer 12 and terminates in a "T" that extends laterally across one end of the tissue-contacting layer 12. Three other electrical conductors, 84, 86 and 88 extend the length of the tissue-contacting layer 12 and terminate at a plurality of points near the termination of conductor 82. The three elements 90 are connected to conductor 82 and to respectively to conductors 84, 86 and 88.

The electrical conductors 82, 84, 86 and 88 required to activate the elements 90 (also called poration elements hereinafter) can be made through the same type of connectors used to interface to the electrical output electrochemical biosensor 28, as described above in conjunction with FIGS. 1–3. Each poration element 90 can be activated individually through the appropriate selection and energization of the conductors 84, 86 and 88. It may be advantageous to excite all poration elements 90 simultaneously, thereby enabling either a series or parallel wiring design, reducing the number of interconnections to the disposable poration system and facilitating a more rapid poration process. If only one element 90 is provided, then at least two conductors are provided for supplying electric current through the heatable element.

These electrically activated thermal poration elements could be installed on a conventionally manufactured assay strip as an additional post-processing step. Preferably, the conductors 82, 84, 86 and 88 are embedded within the tissue-contacting layer so as not to be exposed on the bottom surface thereof, but to enable sufficient electrical connection to the one or more heated elements 90.

Each of the elements 90 functions as a solid thermal probe and is electrically heated so that a temperature of the tissue, if skin, is raised to a temperature greater than 123 C. For example, each element comprises a 100 to 500 micron long 50 micron diameter, gold plated tungsten wire. These tungsten wires are typically laid flat against some form of backing (such as the tissue-contacting layer 12) which naturally limits the depth of penetration of the wire into the tissue (by virtue of the diameter of the wire). The temperature of the wire may be modulated according to the techniques disclosed in co-pending U.S. application Ser. No. 08/776,863.

The inlet ports to the fluid management chamber 9 of the integrated device 70 may small holes in the tissue-contacting layer across which the wires 90 extend. Alternatively, a meltable membrane is placed above the wires 90. When energized, the wires melt a hole in this membrane, creating a inlet port to the fluid management chamber 9 at each location of the wires 90.

A system can be designed wherein the electrically heated poration elements 90 are contained in a separate component or device, which may be reusable. These elements would be replaced when it is detected that they are worn sufficiently to require replacement, or routinely, such as on a weekly basis, similar to a diabetic subject's replacement of a lancet tip in a fingertip lancing blood-drawing device. An indexing mechanism is used to ensure that the micropores are placed in a location that would properly align with the inlet ports of an integrated device. Such a system is described hereinafter in conjunction with FIGS. 18–23.

FURTHER ENHANCEMENTS TO USES OF THE INTEGRATED DEVICE

Figure 11:
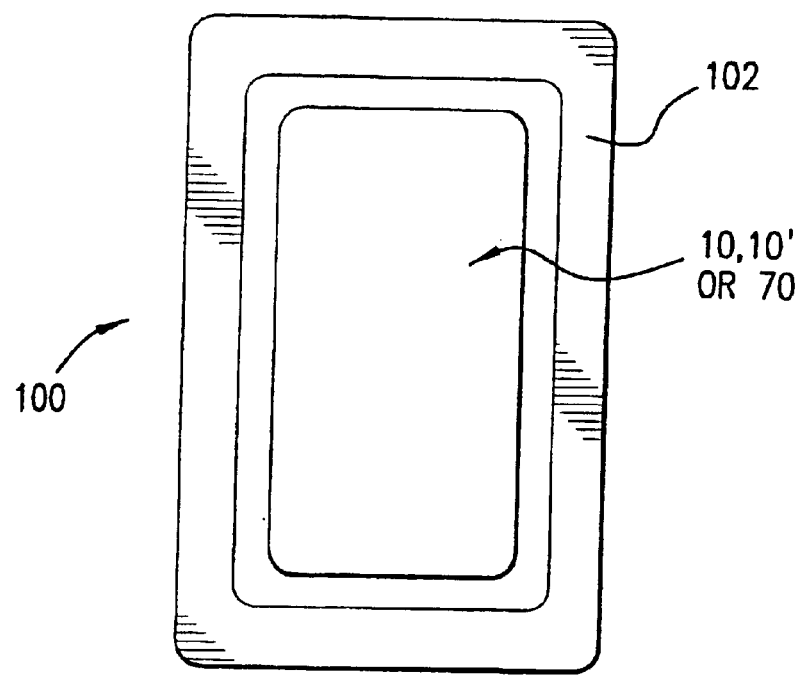
FIG. 11 is a top view of a portion a pneumatic sealing system for use in connection with the integrated device.
Figure 12:
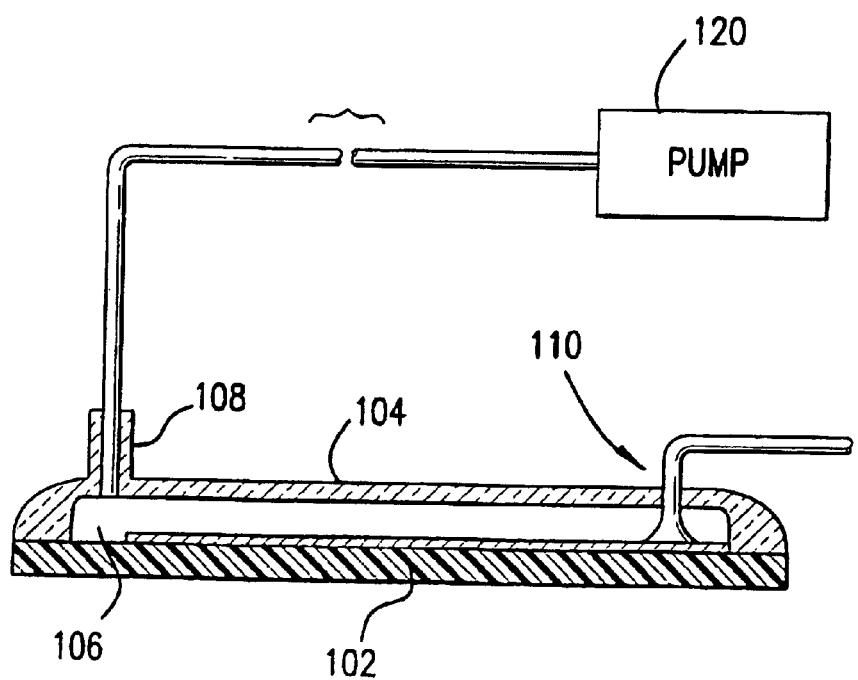
FIG. 12 is a side view of the pneumatic sealing system shown in FIG. 11.

FIGS. 11 and 12 illustrate the use of a pneumatic seal in connection with any one of the integrated devices described above. A sealing means in the form of a sealing assembly 100 is provided which comprises a perimeter base 102 that fits around the integrated device 10, 10' or 70, and a top layer 104 that is sealed to the perimeter base 102, and extends above the integrated device. The sealing assembly 100 pneumatically seals around the integrated device to the surface of the tissue. If the integrated device is of the type that requires exposure to optical energy, the top layer 104 is made of optically transparent material. The perimeter base 102 seals to the tissue surface around the integrated device, such as by an adhesive, or a tacky silicone, rubber or plastic element. A sealed chamber 106 is formed in the space between the integrated device and the top layer 104. A vacuum port 108 is provided in the top layer 104 for connection to a means for supplying negative pressure, such as a pump 120 or other source of negative pressure, such as a syringe, a diaphragm or some portion of the chamber which can be flexed outward to increase the volume of the chamber and thereby reduce the pressure within the chamber or the like. In addition, if an integrated devices is used that requires connection to an electrode on the detecting layer and/or heated probe, this connection is made through a sealed electrical connector 110 in the top layer 104.

The chamber 106 is formed against the surface of the tissue, such as the skin, over the poration site(s). The pressure in the chamber 106 can be reduced to provide a positive pressure gradient from within the body towards the chamber 106 through the micropores to induce the biological fluid to exit the body and enter the assay system more rapidly.

By maintaining the total internal volume of the chamber 106 as small as possible, only providing the needed clearance for the integrated device, the evaporative losses of the biological fluid can be minimized. Essentially, once the humidity inside the chamber 106 reaches a saturation point, no more evaporative losses can occur. These evaporative losses can further be reduced by managing the biological fluid in a manner wherein the exposed surface area of the biological fluid pool that has exited the body is kept small. When induced to enter the device, the biological fluid is constrained on all sides other than the port(s) to the assay area at the microporated site. The side or wall layer of the assay area opposite these ports could be constructed with one or more very small opening(s) to create a vent allowing the biological fluid to fully fill the fluid management chamber, yet minimize the exposed surface of the biological fluid when the assay area is full to reduce evaporation. The reduction of evaporative losses is more significant when using a vacuum-induced harvesting process because the rarefied atmosphere will accelerate any evaporation process. Experiments have shown that simply keeping the volume of the chamber small, and providing some sort of capillary type channel (comprised of the detecting layer on one side and the tissue-contacting layer on the other with or without the optional fluid-transporting layer therebetween) for the biological fluid to enter upon exiting the body, can keep evaporative losses consistently under 5% over a 45 second harvesting cycle, whereas using a large chamber and an exposed bead of biological fluid on the surface of the skin can allow up to 30% of the biological fluid to evaporate during this same 45 second interval under the same temperature and vacuum levels.

An additional feature of pneumatically sealing the integrated device is that by virtue of its contact with the tissue, these portions of the integrated assay system maintain the mechanical alignment of the micropore(s) in the tissue with the biological fluid entry points into the assay system.

Figure 13:
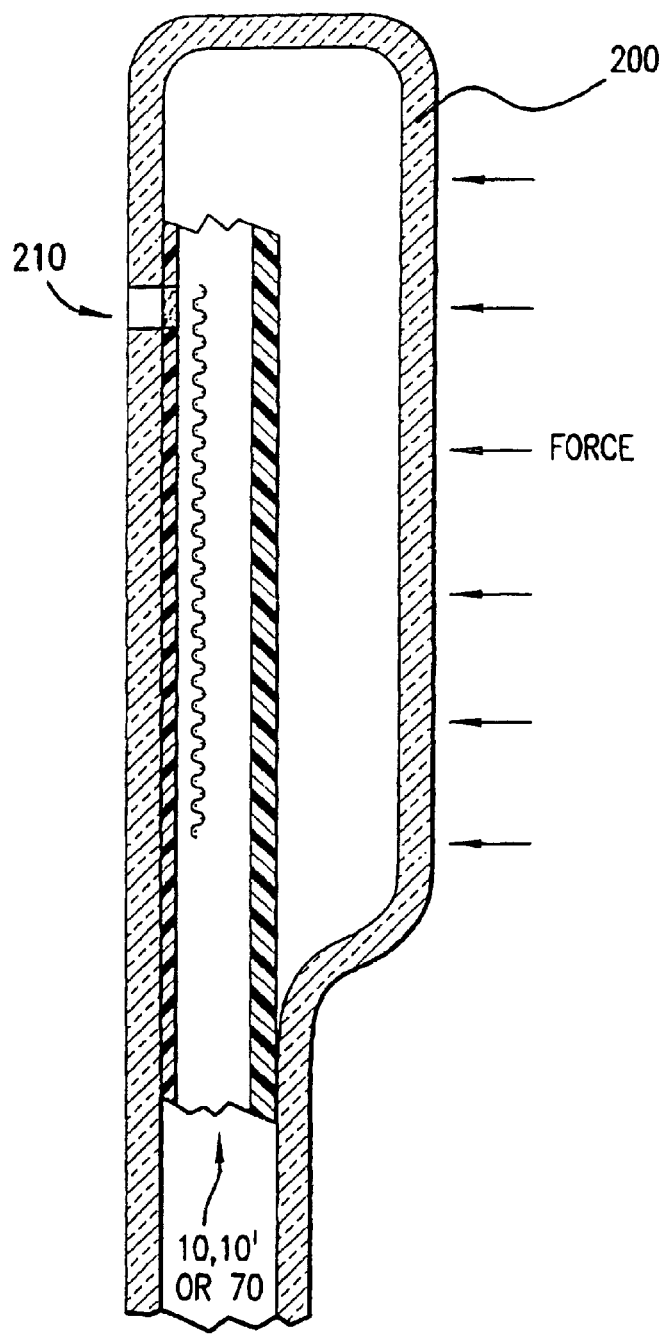
FIG. 13 is an enlarged side view of the use of a mechanical pressure device with the integrated device.
Figure 14:
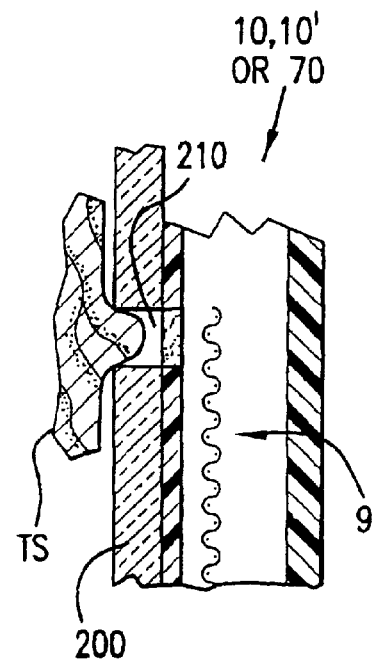
FIG. 14 is an enlarged side view showing the effects of the mechanical pressure device shown in FIG. 13.

FIGS. 13 and 14 illustrate the use of a mechanical system to physically apply pressure to the integrated device. A mechanical element 200 is provided, having a small opening 210, 2 mm to 4 mm in diameter. The mechanical element 200 permits the integrated device to slide between two opposing surfaces and contains the integrated device. Applying force to the mechanical element 200 presses the integrated device onto the skin at the poration site and thus creates a positive pressure gradient in the biological fluid harvested from the tissue TS, i.e., the skin, forcing it towards the micropores where it can exit the tissue and enter the inlet ports of the fluid management chamber 9 of the integrated device. In addition, the tissue bulges into the opening 210. A close registration is maintained between the inlet ports to the assay area of the device and the micropores which have been, or simultaneously will be, formed in the skin directly beneath these ports. If the integrated device is of the type similar to devices 10 or 10', the mechanical device 200 would be optically clear on its top portion to allow for optical thermal ablation and optical reading of the calorimetric assay strip.

The application of mechanically induced pressure may be continuous, modulated as in a sine or triangle wave, or pulsed. The rate and modulation pattern may be optimized to take advantage of the fluidic properties of the skin tissues such as the local permeabilities, and the refill or recovery rates of the tissue once some portion of the biological fluid has been pressed out of it. Clinical experiments have demonstrated that applying a few pounds per square inch of pressure to the skin with a flat plate having a 2 mm to 4 mm diameter hole in it surrounding the micropore(s) rapidly forces biological fluid to exit the pores and pool on the surface of the skin. In addition, the use of the mechanical device may be combined with vacuum to provide an additional biological fluid forcing function, and to possibly assist in the fluid management of the biological fluid as it exits the body. A further benefit of applying firm pressure to the system during the thermal poration process is that this pressure helps ensure a good thermal connection between the heat probe created by the optically heated absorber targets and the skin to be porated. This type of pressure can also be used in connection with the electrically heated probes.

One important requirement of any integrated microporation, harvesting, assay system is that the input ports or channels to the assay system be in physical registration or alignment with the micropores on the skin to ensure an efficient transfer of fluid from the micropores to the assay strip. Registration and alignment can be achieved by employing an adhesive or tacky silicone product to temporarily attach the integrated device. Alternatively, registration and alignment can be accomplished by installing the assay strip component within a translation system which, when activated, brings the input ports or channels of the assay strip into close enough proximity to the biological fluid exiting the micropores to cause the directed flow of this biological fluid into the assay strip. This sort of translation can be achieved in a number of ways such as, but not limited to, a small servo motor activated by a controller to move the assay strip into position at the appropriate time; a pneumatically positioned system driven by the same vacuum source described in conjunction with FIGS. 11 and 12; or a system design wherein the flexure of the skin itself under either the vacuum or pressure as described above brings the biological fluid on the surface of the skin into contact with the assay strip. An additional advantage of the translation system in the fluid management portion of the integrated microporation, harvesting, assay system is that it can be designed to supply the entire required fluid sample in a bolus delivery to the assay system, rather than trickling it over some longer period of time. In many cases a bolus delivery of sample fluid enables a more accurate assay to be conducted using standard disposable assay strip design concepts. A system which facilitates a bolus delivery of a sample fluid is described hereinafter in conjunction with FIGS. 18–23.

Furthermore, by designing the integrated microporation, harvesting, assay system in such a manner that the biological fluid fluid management is handled with minimal dead space outside of the active region of the biosensor, a system can be built which uses very small samples of biological fluid to obtain an accurate assay of a selected analyte. Tests have been conducted on commercially available systems using glucose sensing amperometric biosensors that incorporated all of these features and it was found that the glucose concentration in a sample of biological fluid smaller than ⅓ of a microliter could be quantified, by modifying commercially available glucose test strips. One of the additional advantages gained by using interstitial fluid as the fluid sample for the assay system is the almost total lack of red blood cells in the sample. Most commercial strip based assay systems utilize some means of separating the corpuscular component from a whole blood sample prior to the application of the fluid sample to the assay element. In many cases, this process is performed by the use of some sort of wicking mesh designed to trap the blood cells and let only the serum move through to the assay area. These filtering approaches can use up as much as ⅘ of the original sample volume in the process. By using interstitial fluid, this step is no longer needed. In other words, a typical sample size of 3 to 10 microliters is normally required for a blood based glucose monitoring disposable assay strip design whereas by utilizing the ability to place an unfiltered interstitial fluid sample directly on the active reagent treated portion of an assay system, it has been demonstrated that quantitative readings of a selected analyte can be obtained with fluid samples as small as ⅓ μL of interstital fluid using conventional disposable assay strip technologies.

Figure 15:
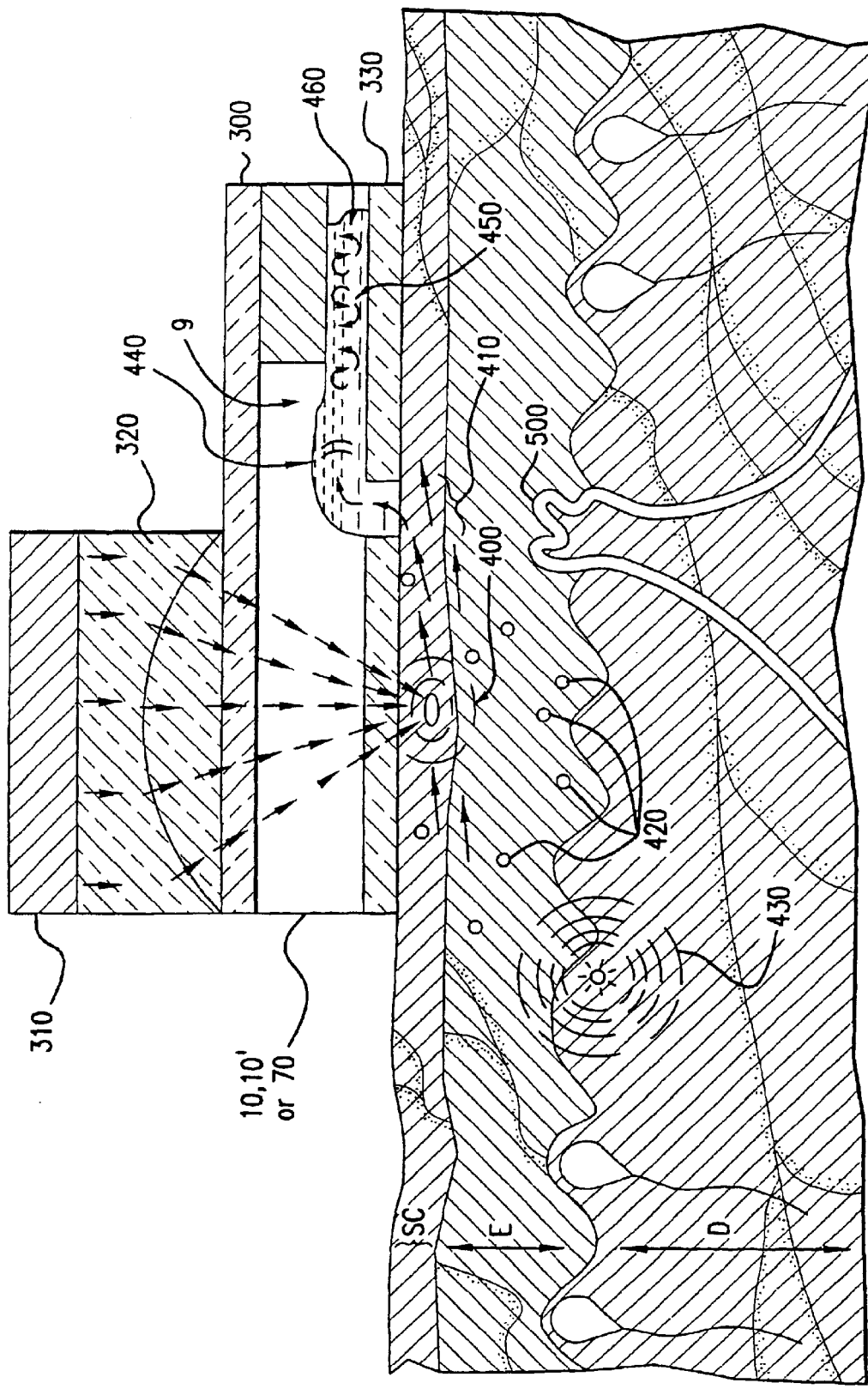
FIGS. 15 and 16 are schematic diagrams showing the application of sonic energy in conjunction with the integrated device.
Figure 16:
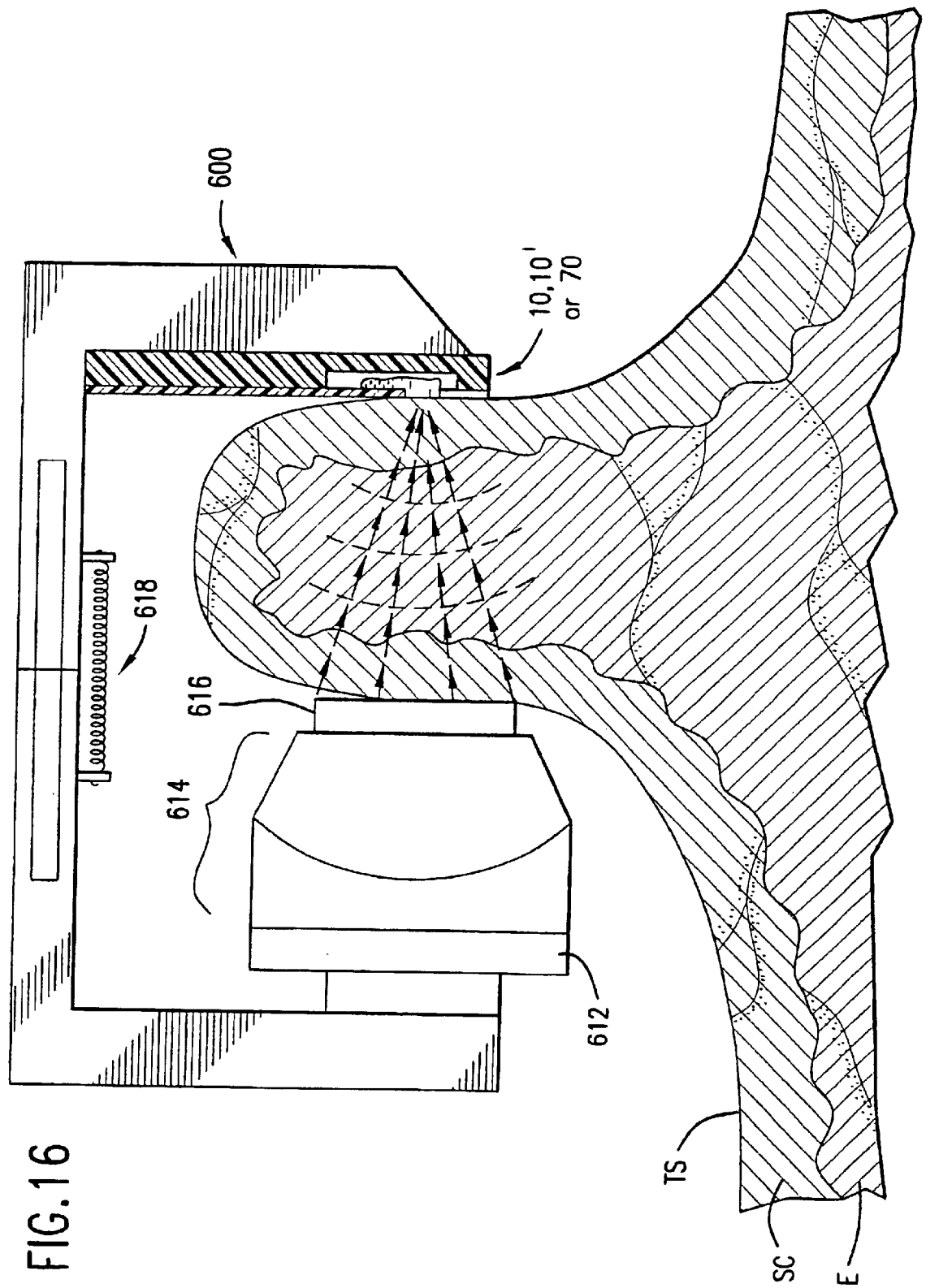

Turning to FIGS. 15 and 16, the use of sonic energy in conjunction with the integrated device will be described. The integrated device can be used in conjunction with a means for coupling sonic energy from a transducer into the system and optionally into the tissues upon which the integrated system is disposed. In particular, experiments have shown that sonic energy in the range of 5 kHz to 30 MHz can be useful to enhance the outflux of biological fluid from a microporated area of skin. Furthermore, the literature on the use of sonic energy supports the extension of the useable frequencies as high as 500 MHz.

The permeation enhancing effect of sonic energy is due to several different mechanisms in the tissue, including but not limited to, the acoustic streaming induced in the fluids within the skin tissues, the reduction in the viscosity of the fluid itself, the modification of the surface tension effects both within the tissues and at the surface of the micropore, the local heating possible from the absorption of the sonic energy and the body's natural edemic response to this, the opening of microscopic temporary channels in the various membranes and layers within the tissue such as the capillary and vessel walls, and the simple physical shaking of the system possible with various pulsed and modulated patterns of sonic energy, and the like.

When incorporating a sonic energy source into a system such as this, it is important to consider the acoustic impedance of the various layers through which the sound waves travel, and the matching of the acoustic impedance at the interfaces of the various layers. For diagnostic ultrasound, a gel is frequently used to facilitate the coupling of the sonic energy into the tissue and this approach could be used to mate the bottom surface of the integrated device element to the surface of the tissue, such as skin. An alternative solution to the coupling issue that eliminates the need for a coupling gel, is to use an appropriately designed gasket type of material, such as a silicone or hydrogel to form the sonic connection. In addition, tacky or adhesive elements are useful to both seal a fluid management chamber and maintain registration between the micropores and the inlet port of the assay system. This elements are also useful as efficient acoustic coupling agents.

In the case where a focused acoustic field is desired, multiple selectively phased sources, sonic lenses or reflectors could all be employed to generate the desired energy distribution within the target zone. A purposefully created impedance mismatch within the media through which the sound waves propagate can be used as a means of forming a reflective boundary. Basically, all traditional wave propagation equations hold true for sonic energy, just as they do for electromagnetic energy, and as such the same type of wave guide or energy directing methods can be employed to focus the sonic energy where desired.

The schematic representation in FIG. 15 shows an integrated device 10, 10' or 70 having a compliant layer 300 placed on the top to form an efficient coupling for sonic energy. Alternatively, the meter-interface layer 20 may be formed of compliant material suitable for coupling acoustic energy to the tissue. The sonic energy is generated by sonic energy generation means, such as a piezo-electric transducer 310. A sonic lens element 320 is placed between the piezo-electric transducer 310 and the compliant layer 300. A coupling gasket 330 may also be provided to pneumatically seal the integrated device to the surface of the tissue (with optional application of suction) and to assist in the acoustic coupling of the sonic energy.

The acoustic waves can be optimized to have any of several recognized actions and effects on the performance of the harvesting and analysis of biological fluid, or delivery of bio-active agents. The sonic energy can be propagated through the integrated device, through the coupling gasket 330, to the tissue (such as skin), wherein SC denotes the stratum corneum, E denotes the epidermis and D denotes the dermis.

Within the tissue, the direct effects of the sonic energy include local warming of the tissue through the direct absorption of the sonic energy. This is shown at reference numeral 400. Depending on the frequency selection and possible modulations of the frequency and amplitude of the sonic energy, an acoustic streaming effect can be achieved within the tissue, accelerating the fluidic movement between cells and within cells and vessels. This is shown at reference numeral 410. The amount of increase in the local velocity of the fluid has been shown to be more than one order of magnitude using visible tracers in in vivo real-time video microscopy experiments.

Similarly, when the frequency and intensity and possible modulation thereof are selected appropriately, a cavitation effect shown by cavitation bubbles at reference numeral 420, is achieved which can have substantial secondary effects on the tissue properties due to possible microscopic shearing of some tissue structures, the transitory opening up of microporous sites in various membranes such as the capillary walls 500 within the tissue, and other effects due to the shock waves, shown at reference numeral 430, created upon the collapse of the cavitation bubble.

The presence of the acoustic vibrations within the fluid management chamber 9 of the integrated device itself can also be used to enhance the motion of the fluid. These effects can be due to a directed radiation pressure gradient shown at reference numeral 440 which can be created by proper alignment and focusing of the sonic energy, the enhancement of capillary transport action shown at reference numeral 450 by the acoustic energy, the active out-gassing of dissolved gas in the fluid which can help to eliminate error causing bubbles in the active assay area of the system, and the localized and chaotic micro-fluidic vortices shown at reference numeral 450 created within the fluid management chamber 9 which can be used to reduce the required assay reaction time by eliminating the dependency on passive diffusion effects and thereby evenly distribute the reactive process within the sample.

The activation of the sonic energy source can be selectively controlled to work in a coordinated fashion with the other components of the system, even to the point of operating with significantly different parameters during different portions of the poration, harvesting, assay process. For example, a sequence of sonic energy use is:

1. Start with a controlled burst of higher energy ultrasound designed to temporarily permeabilize the capillary walls and the intervening bulk tissue structures during the poration cycle. The presence of this type of short pulse of high intensity sonic energy has also been shown to reduce the perceived sensation associated with the thermal poration process by most subjects.

2. During the fluid collection phase, a lower power, swept frequency modulation setting of the sonic energy could be used to induce the acoustic streaming effect within the tissue designed to bring more biological fluid to the surface.

3. As the biological fluid exits the body and enters the inlet port of the assay system (the integrated device), the sonic energy could be re-tuned to more optimally enhance the surface tension driven transport of the biological fluid towards the active reagent area, biological fluid transport could be used both within a capillary channel, a mesh or a porous media transport layer system.

4. Once on the active reagent layer, the operating parameters of the sonic energy could once again be adjusted to create the active "stirring" of the fluid within the fluid management chamber to facilitate a more rapid and/or accurate quantification of the selected analyte.

Essentially all of the same functional modalities described in conjunction with FIG. 15 can also be realized with an alternative configuration wherein a remotely placed sonic source is used to direct the acoustic energy towards the desired portion of the assay element of the integrated device by beaming it through a fold of intervening flesh.

With reference to FIG. 16, a clamp assembly 600 is provided to pinch a fold of tissue, such as skin between a transducer assembly shown at reference numeral 610. The transducer assembly 610 comprises an acoustic transducer 612, a focusing element 614, and a coupling layer 616. The integrated device 10, 10' or 70 is at an opposite side of the pinch of skin. The dimensions of the clamp assembly 600 are such that when the tensioning device 618 pulls the two clamp halves together, they hit a hard stop and the spacing from the face of the transducer assembly and the inlet port of the fluid management chamber of the integrated device is positioned at an optimal position in {x, y, and z} coordinates to coincide with the sonic energy fields as desired. For example, FIG. 16 shows the focal point of the sonic field is roughly coincident with the inlet port of the assay chamber, which may be one selected mode of operation. However, by shifting the frequency of the sound waves, this focal point can be moved in and out from the face of the transducer.

Experiments have shown that it can be advantageous to modulate the frequency, thereby shifting the sonic energy field position and local intensities. This sort of control of sonic energy fields has been shown to induce an active pumping action at the modulation rate of the system which can similarly be used to exploit certain fluid and mechanical properties of the tissues.

By employing a clamping mechanism which forces the sonic transducer against the skin surface, the coupling losses at this interface can be reduced and/or controlled within a design specification.

The initial deflection into the inter-clamp space can be accomplished by placing the entire assembly within a suction system, such as that shown in FIGS. 11 and 12, which pulls the flesh into the space, and as the vacuum increases, provides the clamping force to pull the two halves of the clamp assembly together to the stops. Similarly this could be accomplished via mechanically feeding a pinch of skin into the space and then letting the clamp grab the tissue.

An additional function of sonic energy applicable to all of the previously discussed sonic enhancement concepts is the demonstrated beneficial effects it can have on the wound healing process. Clinical results have consistently shown positive effects when sonic energy is applied to various types of wounds including bums and other superficial skin traumas. In the case of microporation created in the outer layers of the skin, this acceleration of the healing process can be exploited to improve the overall acceptance of the system by the end user and health care practitioners.

CONSTRUCTING THE INTEGRATED DEVICE

The device 10 or 10' is preferably mass-produced. However, the following method is provided for illustrative purposes.

The meter-interface layer 20 is provided in the form of a sheet. In a typical construction, the meter-interface layer 20 is a sheet of polyvinyl chloride. The detecting layer 28 is screen printed onto the meter-interface layer 20. In the embodiment where the detecting layer 25 is an electrochemical biosensor 28, a biosensor of a type described in U.S. Pat. No. 4,545,382, which is incorporated herein by reference, is used. The electrochemical biosensor 28 contains a biologically active substance that reacts with glucose, preferably glucose oxidase or glucose dehydrogenase, at an electrically conductive material, preferably carbon, which carries the electrical signal produced by the reaction of glucose with the biologically active substance. The generation of the electrical signal may be aided by compounds known as mediators, which increase the electrical signal. For example, see "Ferrocene-Mediated Enzyme Electrode for Amperometric Determination of Glucose", Anal. Chem. 1984, 56, 667–671. The electrical circuit is completed with at least one other electrically conductive material, preferably carbon. The fluid-transporting layer 18 is then placed in a position such that it will be in fluid communication with the electrochemical biosensor 28. The overcoat layer 16 is then screen printed onto the meter-interface layer 20 and cured in a curing oven. A template or the like can be used so that the cured overcoat layer does not block the interstitial fluid from reaching the fluid-transporting layer 18. Finally, the tissue-contacting layer 10 is applied over the overcoat layer 16 and bonded to the overcoat layer 16, preferably by a thermally curable adhesive or a thermally setting adhesive.

OPERATION OF THE INTEGRATED DEVICE

Figure 17A:
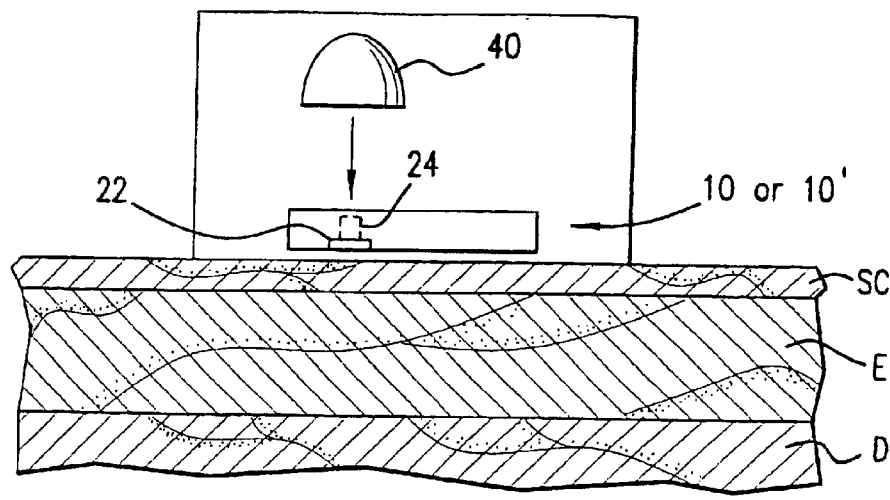
FIGS. 17A, 17B, and 17C illustrate the use of the device according to the present invention.
Figure 17B:
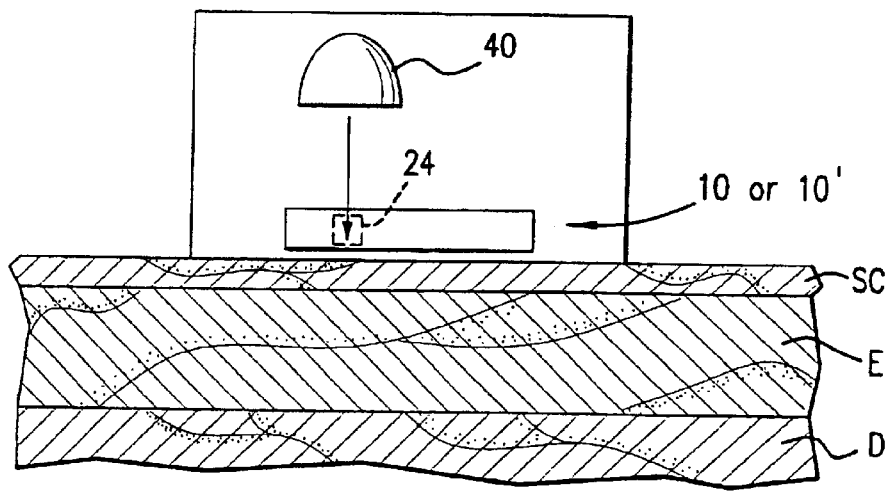
Figure 17C:
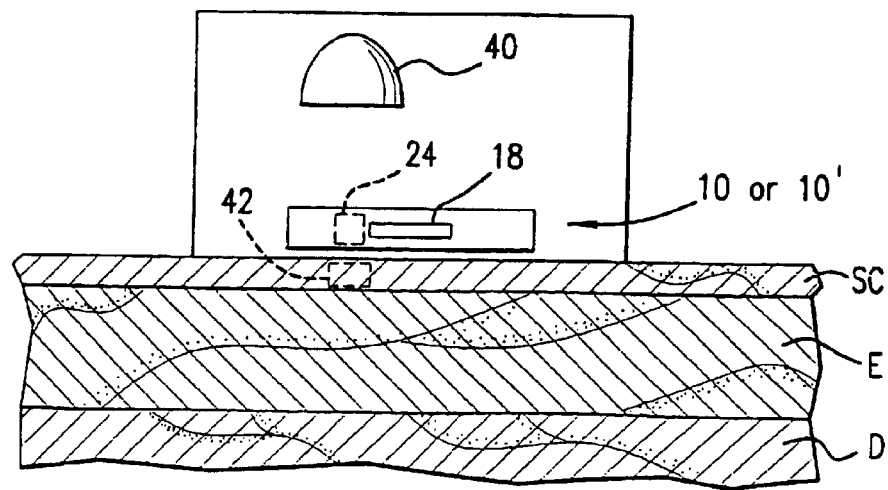
Figure 18:
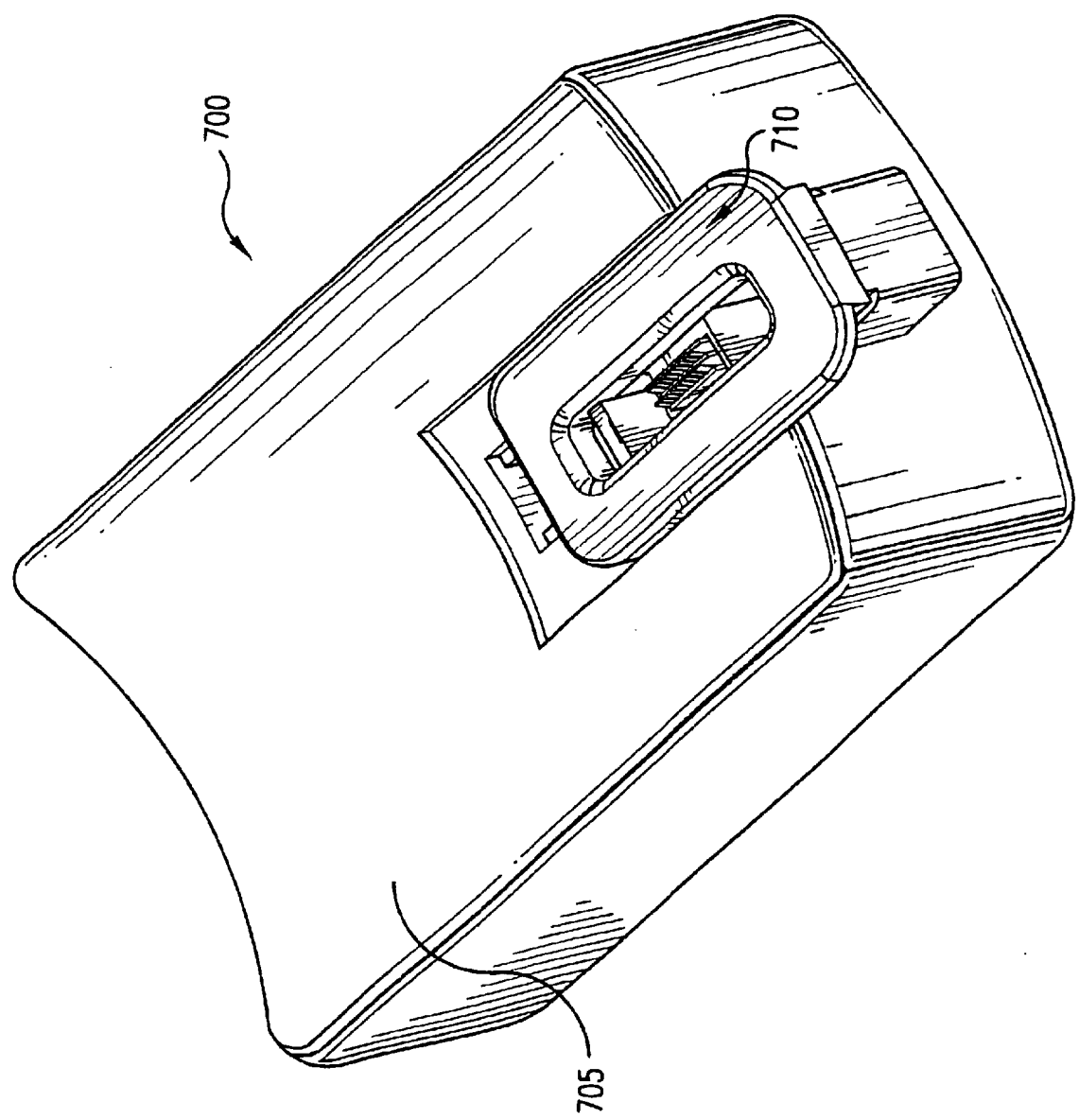
FIGS. 18–21 illustrate a portable glucose monitoring system which uses a disposable assay strip and a limited re-usable porating head, in accordance with still further embodiments of the present invention.

FIGS. 17A, 17B and 17C illustrate the operation and use of an device 10 or 10'. In order to detect the presence, level or concentration of analyte in a sample of interstitial fluid, the major surface 15 of the tissue-contacting layer 12 of the device 10 is placed against a surface of the tissue, such as skin. In operation, a source of optical energy 40, such as a pulsed laser, is activated. The energy from the source 40 is transmitted through the opening 24 in the device 10 and strikes the target portion 22. After an appropriate period of time, e.g., from about 10 ms to about 1 second, the energy generated by the light source 40 heats the target portion 22, and the thermal energy in the target portion 22 is transferred to the skin to ablate the skin and form at least one micropore 42 as shown in FIG. 17C. Typically, many such micropores 42 are formed. The micropore 42 may partially or completely extend through the stratum corneum, but in most cases will terminate before reaching the dermis. Optionally, if the micropore 42 extends through the dermis, the biological fluid collected will be blood. The biological fluid traverses the stratum corneum through the micropore 42 and is taken up by the fluid-transporting layer 18. The biological fluid flows through the fluid-transporting layer 18, whereupon it reaches the electrochemical biosensor 28 or colorimetric sensor 30, depending on which detecting layer 25 is used.

A chemical reaction occurs at the detecting layer 25. The output of the chemical reaction is read by a meter 50 or 50'.

Sources of electromagnetic energy that are suitable for use with the device 10 of are disclosed in U.S. patent application Ser. No. 08/776,863.

In summary, the device 10 or 10' is an integrated poration, harvesting and analysis device, comprising a tissue-contacting layer having a target portion thereon which is responsive to electromagnetic energy to heat and conduct heat to the tissue to form at least one opening, such as a micropore, therein; a fluid-transporting layer adjacent the tissue-contacting layer capable of transporting biological fluid from the tissue; and a detecting layer in fluid communication with the fluid-transporting layer and responsive to the biological fluid to provide an indication of a characteristic of the biological fluid. The detecting layer comprises an electrochemical biosensor or a calorimetric sensor. The fluid-transporting layer is treated with a chemical to enhance the wicking capabilities of interstitial fluid.

Furthermore in one embodiment, the target portion on the tissue-contacting layer comprises a quantity of photosensitizing material, combined with a carrier such that the photosensitizing material is substantially uniformly dissolved or suspended therein, wherein the tissue-contacting layer serves as a substrate for the carrier-photosensitizing material combination. In another embodiment, the target portion comprises a substantially uniform suspension of photosensitizing material in a film material which forms the tissue-contacting layer.

The operation of the device 70 involves the application of electrical current to the poration elements. The biological fluid is then collected through the micropores in the same manner as described above.

The operation of the devices 10, 10' and 70 can be enhanced by the other various techniques described above, including pneumatic sealing, mechanical pressure, etc.

Figure 19:
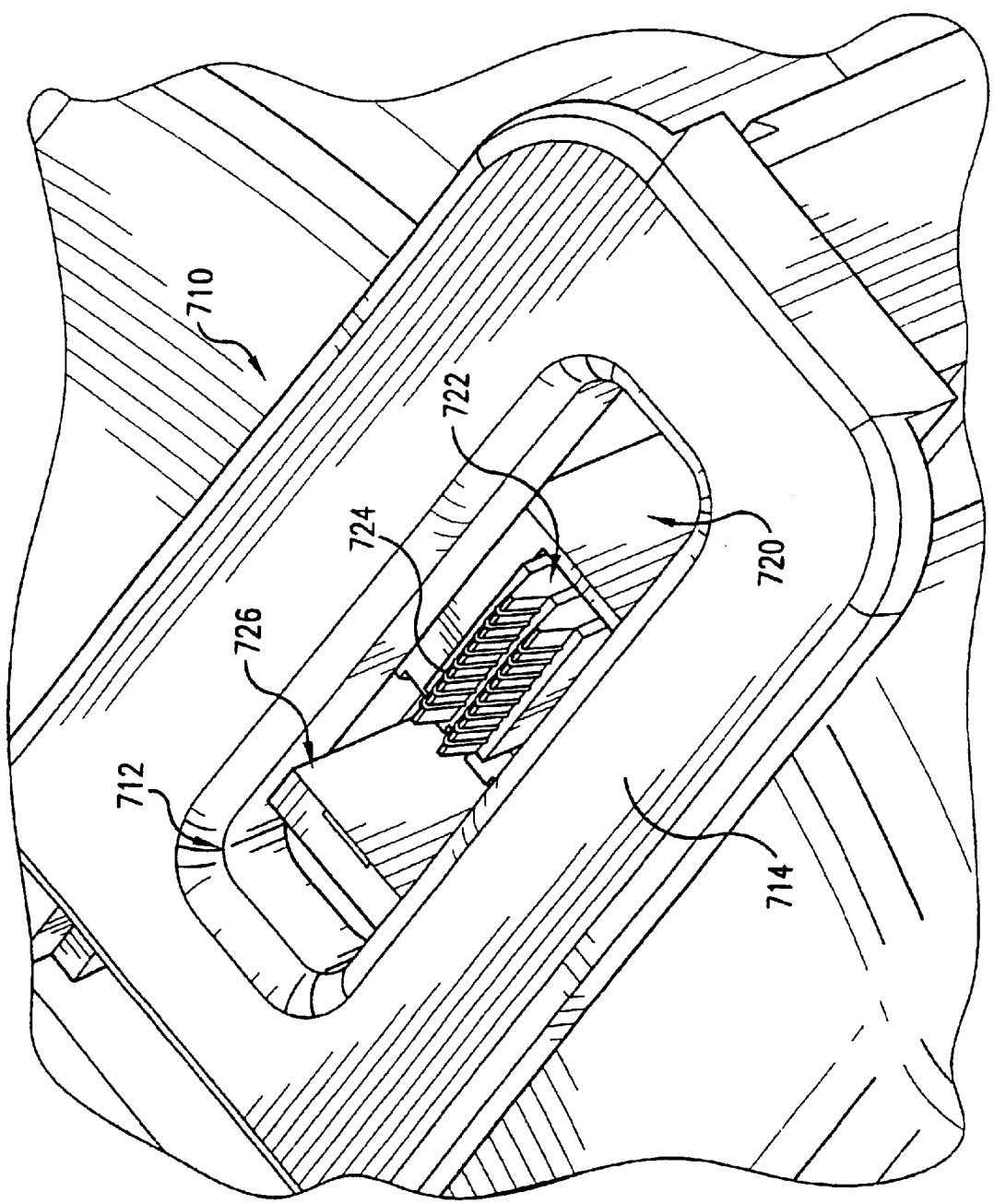
Figure 20:
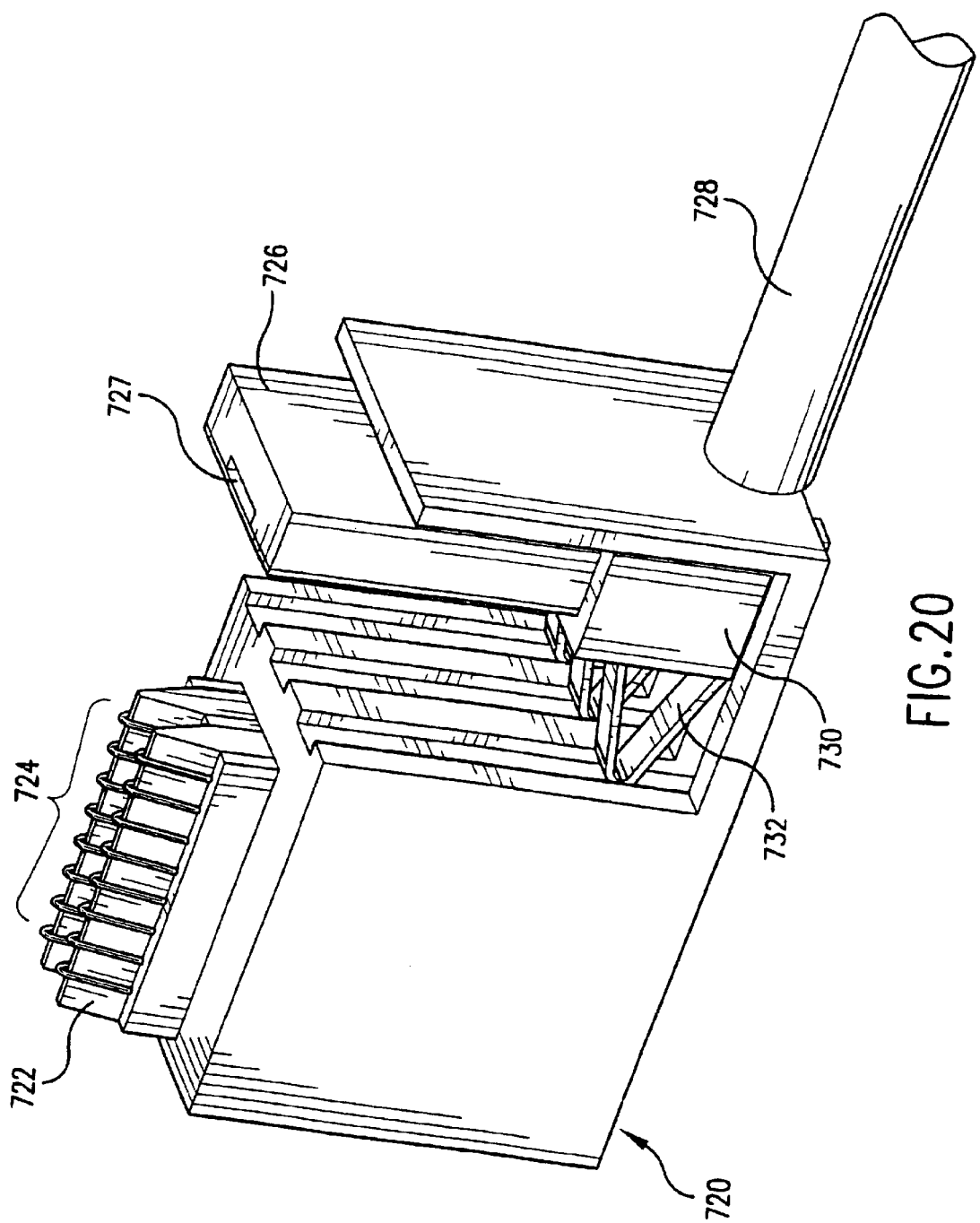

FIGS. 18–21 illustrate a portable (hand-held) glucose monitor device according to another aspect of the present invention. The monitor device, shown generally at reference numeral 700, comprises a vacuum chamber mechanism 710 against which a user places a forearm, thigh, waist, or other skin surface. A contoured surface 705 is provided on the monitor 700 to facilitate engagement of the vacuum chamber mechanism 710. As shown in FIG. 19, an elongated opening 712 is provided on the vacuum chamber mechanism to mate with the skin surface. A porator/assay carriage 720 is mounted within the vacuum chamber mechanism 710. The porator/assay carriage 720 supports a porator head 722 having a plurality of electrically heated elements (porator elements) 724, and a disposable glucose assay strip 726. The assay strip 726 is held in position on the porator/assay carriage 720 by an assay strip holder 730, which includes electrical contacts 732 to the assay strip 726 (three contacts are shown, as an example).

Figure 21:
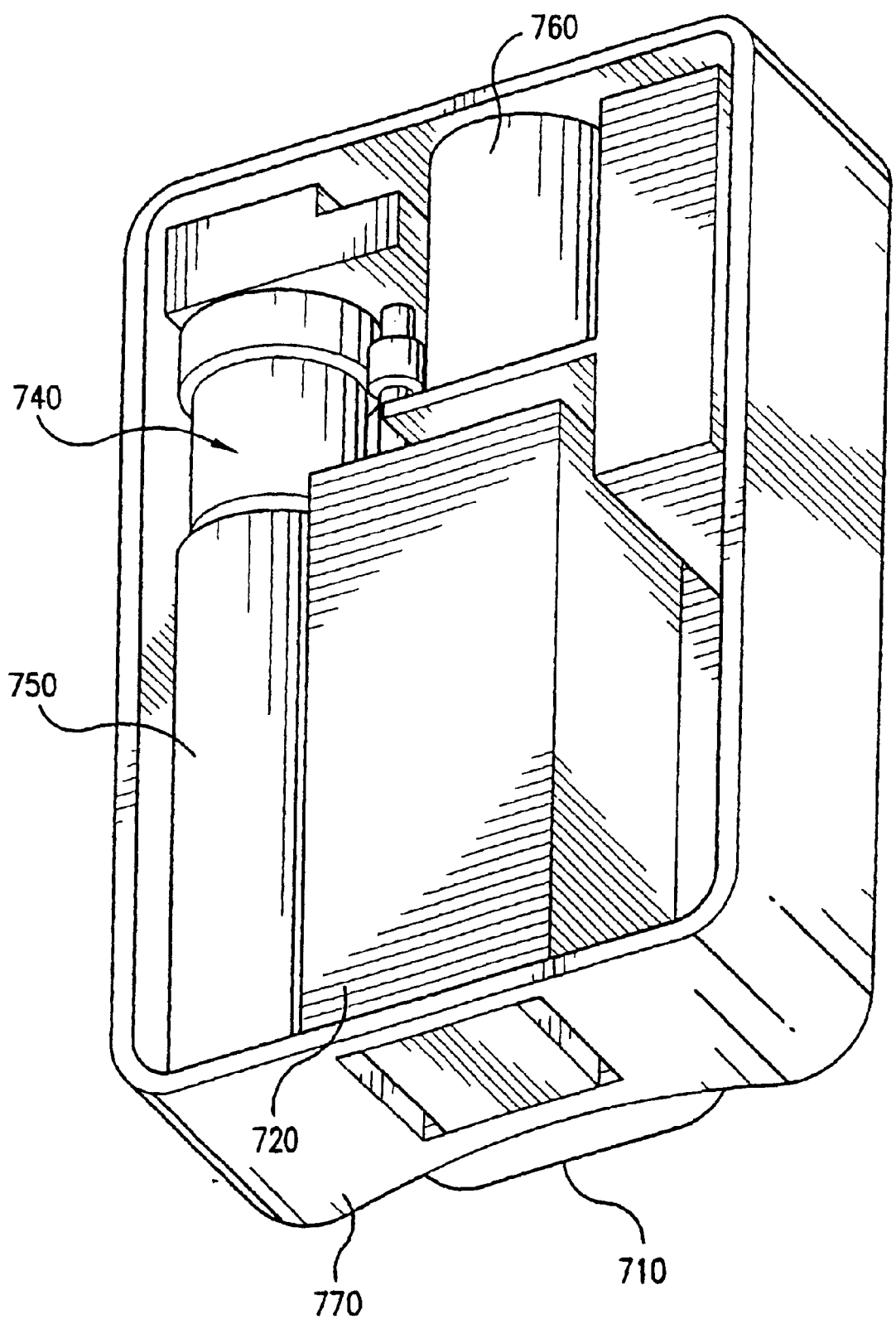

As shown in FIG. 21, the monitor 700 further includes a vacuum pump 740, a battery power supply 750, and a motor 760 all contained within a lower housing 770 of the monitor 700.

The vacuum chamber mechanism 710 has a sealing ring or gasket 714 formed of suitable material to seal the vacuum chamber to the skin of a user. The vacuum chamber mechanism 710 has retracted operating position and an extended position. The extended position, shown in FIG. 18, facilitates removal of the vacuum chamber mechanism 710 for replacement due to contamination, wear, inability to maintain a vacuum seal, etc. This replacement will possibly occur periodically, such as every six months.

The porator head 720 is a multi-use item, but would require replacement after a predetermined number of uses. Two linear poration arrays are shown side-by-side. These two heads would microporate the skin in a sixteen (two by eight) pore pattern which is narrow enough to allow collecting all of the fluid presented at the pores by translating the assay strip in one direction.

The assay strip 726 comprises a small rectangular opening 727 at the end which draws the biological fluid into the strip 726 via capillary action. This assay strip is a one-time use only item. Typically, the monitor checks 700 for a previously used strip before beginning the monitoring process. The strip has a tiny (one to five microliters) assay chamber built in, as well as integral conductive paths.

The motor 760 moves the porator/assay strip carriage back and forth within the vacuum chamber mechanism 710.

In operation a user loads a new assay strip 726 into the assay strip holder 730 in the porator/assay strip carriage 720 by turning the monitor 700 over and inserting the strip through the opening in the lower housing 770. If necessary, the porator head 722 would be replaced in a similar manner. The monitor 700 includes processing intelligence to alert the user when the porator head or heads 722 requires replacement. The user then places the vacuum chamber mechanism 710 against the skin at the testing site (forearm, thigh, waist, etc). The user presses a button on the monitor 700 to start the monitoring process. When this button is pressed, the strip 726 is tested for correct insertion, no prior use, compatibility, etc. If the strip 726 is viable, the vacuum pump 740 engages and pumps most of the air out of the vacuum chamber. Once the chamber is evacuated, the surface of the skin is temporarily but securely registered to the lower surface of the chamber 720 and pulled up into light contact with the poration head 722. After the skin contacts the poration head 722, electrical current is applied in short pulses, sequentially and rapidly to each element 724 in turn. A micropore is thereby formed at the tip of each element 724. As soon as the last pore is formed, the porator/assay strip carriage 720 is advanced within the vacuum chamber by the motor 760 coupled to the arm 728 of the carriage until the pores lie in the space between the poration head 722 and the assay strip 726 providing clearance so that the biological fluid can accumulate without being prematurely wicked away. Alternatively, the vacuum level could be reduced to allow the surface of the skin to pull a slight distance away from the poration head 722 to provide clearance for the biological fluid to accumulate. The vacuum is maintained for a short time (perhaps thirty seconds to one minute) which causes a biological fluid bead to form at each pore on the surface of the skin. Once sufficient time has elapsed for enough biological fluid (one microliter) to accumulate, the porator/assay strip carriage 720 is advanced by the motor 760 so that the opening 727 of the assay strip 726 comes in contact with each bead of biological fluid, drawing the biological fluid into the assay strip 726 through capillary action. The biological fluid is therefore effectively delivered to the assay chamber of the strip 726 as a bolus. When the strip 726 is full, which can be detected through the use of the integral conductive sensor paths, the harvesting process can be terminated, and the vacuum released. The monitor 700 can then be removed from the surface of the skin. A period of time (fifteen to thirty seconds) after the bolus of biological fluid fills the assay chamber of the strip 726 is typically required to calculate a glucose level.

Figure 22:
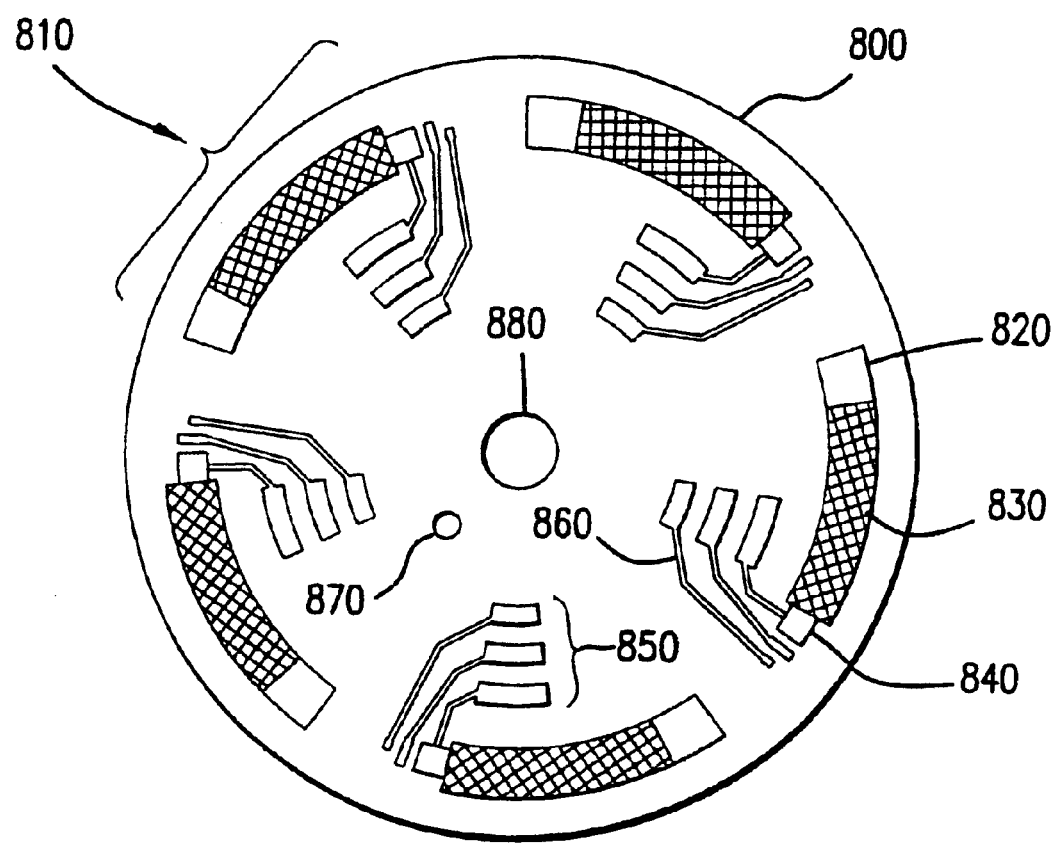
FIG. 22 illustrates a disk cartridge supporting multiple assay elements each containing microporation, fluid accumulation and assay areas for use together with a glucose monitoring device, according to yet another embodiment of the present invention.

Turning to FIG. 22, a rotary assay cartridge system, which is also capable of supplying a bolus of biological fluid sample for analysis, is described. A disk-shaped assay cartridge, shown generally at reference numeral 800 is provided. The assay cartridge 800 consists of several separately usable assay elements 810 mounted to the same disk cartridge. The cartridge is about 25 to 50 mm in diameter, and less than one millimeter thick. FIG. 22 shows five separate assay elements, but the total number is a function of the size of each assay element and the desired size of the cartridge 800.

Each assay element comprises a dye layer or target 820, a biological fluid accumulation area 830, and an assay pad 840. The dye layer 820 may comprise a photosensitizing assembly described above, and is held against the skin and serves as the heat source for thermal ablation in response to optical energy. Alternatively, a plurality of electrically heated elements could be disposed on the portion of the assay element where the dye layer is shown, such as shown in FIGS. 9 and 10. Preferably, the dye layer is large enough to support a 2×8 array of micropores formed therethrough at sufficient spacing.

A biological fluid accumulation area 830 is provided. This area actually consists of holes or mesh in the disk 800. After the pores are formed, the disk 800 is rotated until the pores lie in this area providing clearance so that the biological fluid can accumulate without being prematurely wicked away.

The assay pad or chamber 840 has a small opening which is presented to the bolus of biological fluid. The biological fluid is drawn into this assay chamber (that is, onto the assay pad) through capillary or wicking action.

Conductive pads 850 terminate the conductive traces 860 on each assay element. The conductive pads 860 are contacted at some point in the process by metal wiper contacts to read the results of the chemical process on the assay pad 840, by which a measurement of an analyte, such as glucose, can be made.

The disk cartridge 800 has a drive and registration hole 870. This hole serves as a convenient point to reference the various areas in each assay element 810. The relationship between the registration hole and the assay elements 810 is constant from cartridge to cartridge. This hole or a similar one could also be used to push against when rotating the cartridge, about an axis 880

In operation, a user loads a new assay cartridge 800 into a glucose monitor (not shown). When the user desires to take a glucose measurement, the monitor would rotate the cartridge 800 until the dye target 820 were at the focal point of the optical energy source and flat against the surface of the skin. The optical energy is delivered, and the skin is porated. As soon as the last pore is formed, the cartridge is rotated within the monitor until the pores lie in the biological fluid accumulation area 830, providing clearance so that the biological fluid can accumulate without being prematurely wicked away. A vacuum causes a biological fluid bead to form at each pore on the surface of the skin. Once sufficient time has elapsed for enough biological fluid to accumulate, the cartridge 800 is further rotated so that the opening of the assay chamber 840 comes in contact with each bead of biological fluid, drawing the biological fluid into the assay chamber 840 through capillary action. The biological fluid is therefore effectively delivered to the assay chamber as a bolus. When the chamber is full, which can be detected through the use of the integral sensor conductive pads, the harvesting process can be terminated, and the vacuum released. The advantage of having multiple assay elements on a cartridge is that the user would only have to load the cartridge once, rather than having to reload a strip each time the monitor is used.

Several aspects of the invention are summarized below. In accordance with one aspect of the present invention, a device and method for porating, harvesting, and analyzing biological fluid from tissue is provided, comprising steps of: contacting or touching a probe to a surface of the tissue; applying energy to the probe so that it heats up and transfers heat to the surface of the tissue thereby forming at least one micropore in the tissue; collecting biological fluid from the tissue through the at least one micropore with a fluid-transporting layer suitable for transporting the biological fluid to a predetermined surface portion thereof; placing a detecting layer in fluid communication with the fluid transporting layer for detecting a characteristic of the biological fluid. A concentration of an analyte in the biological fluid may be measured based on electrical characteristics of the detecting layer or optical characteristics of the detecting layer. The device may comprise a tissue-contacting layer having a probe thereon suitable for conducting heat to a surface of the tissue to form at least one opening therein; and a detecting layer in fluid communication with the at least one opening formed in the surface of the tissue, the detecting layer being responsive to the biological fluid to provide an indication of a characteristic of the biological fluid.

In accordance with another aspect of the invention, sonic energy is delivered throughout various stages of a microporation, harvesting, analysis process. The sonic energy is coupled through an integrated device for performing these functions, and the parameters of the sonic energy are adjusted at each stage of the process to appropriately enhance each stage.

In accordance with still another aspect of the invention, a system is provided by which a portable glucose monitor can interface with a disposable device that facilitates the microporation, harvesting of biological fluid, and analysis of the biological fluid. More specifically, this system facilitates the delivery of biological fluid in a bolus to an assay strip or similar device so that overall, a smaller volume of biological fluid is needed to perform the assay and obtain a reliable reading.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An integrated assembly for treating tissue, comprising: (a) a quantity of photosensitizing material; (b) a carrier which is combined with the photosensitizing material such that the photosensitizing material is dissolved or suspended therein; and (c) a substrate to which the carrier-photosensitizing material combination is applied including a tissue contacting layer having a target portion and a fluid transporting layer adjacent said tissue contacting layer and aligned with the target portion, said target portion capable of receiving electromagnetic energy and converting it into thermal energy for tissue poration.

2. The assembly of claim 1, and further comprising a layer of priming material between the substrate and the carrier.

3. The assembly of claim 1, wherein the photosensitizing material is a dye or a pigment.

4. The assembly of claim 1, wherein the carrier is one of a solid polymer, adhesive, gel and ink.

5. The assembly of claim 1, wherein said target portion is capable of converting laser energy into thermal energy.

6. The assembly of claim 5, further comprising a detection layer having an electro-chemical biosensor which is responsive to the fluids received from the tissue.

7. An assembly for porating tissue, comprising: (a) a quantity of photosensitizing material, said material capable of converting laser energy into thermal energy; and (b) a film material containing a substantially uniform suspension of the photosensitizing material comprising a target area for receiving laser energy and porating tissue by heating.

8. The photosensitizing assembly of claim 7, and wherein the film material is made of one of polyesters, polyimides, polyethylenes, polypropylenes, acrylics, cellulose and derivatives thereof.

9. The photosensitizing assembly of claim 8, wherein the photosensitizing material is a dye or pigment.

10. An integrated poration, harvesting, and analysis device comprising the photosensitizing assembly of claim 7, wherein the device comprises: (a) a tissue-contacting layer having a target portion comprised of the photosensitizing assembly;

and (b) fluid-transporting layer adjacent the tissue-contacting layer and aligned with the target portion.

11. The device of claim 10, and further comprising a meter-interface layer adjacent the fluid-transporting layer.

12. A method of porating tissue comprising the steps of: (a) applying a photosensitizing assembly including a quantity of photosensitizing material to the tissue; and (b) subjecting said photosensitizing assembly to electromagnetic radiation to cause thermal ablation of the tissue.

13. The method of claim 12, wherein the step of applying comprises applying a substrate to which is applied a carrier in which the quantity of photosensitizing material is substantially uniformly dissolved or suspended.

14. The method of claim 13, wherein the step of applying comprises adhering the substrate to the tissue.

15. The method of claim 12, wherein the step of applying comprises applying a film incorporating a substantially uniform suspension of the photosensitizing material.

16. The method of claim 12, wherein the electromagnetic radiation is in a wavelength range from about 10 nm to about 50,000 nm.

17. The method of claim 12, wherein said step of subjecting comprises emitting electromagnetic radiation from a polychromatic light source.

18. The method of claim 12, wherein said step of subjecting comprises emitting electromagnetic radiation from a laser.

19. The method of claim 12, and further comprising the step of withdrawing body fluids from an opening created in said tissue.

20. The method at claim 19, and further comprising the step of determining the concentration of at least one analyte in the body fluids.

21. The method of claim 20, wherein the step of determining comprises determining the concentration of glucose.

22. The method of claim 12, and further comprising the step of introducing a permeant into an opening created by said ablation.

23. An integrated poration, harvesting and analysis device, for porating tissue, comprising: (a) a tissue-contacting layer, a heat generating probe in thermal communication with the surface of the tissue to form at least one opening therein; and (b) a detecting layer in fluid communication with the at least one opening formed in the surface of the tissue, the detecting layer being responsive to a biological fluid collected from the tissue to provide an indication of a characteristic of the biological fluid.

24. The device of claim 23, wherein the probe is capable of being heated such that the temperature of tissue-bound water and other vaporizable substances in a selected area of the surface of the tissue is elevated above the vaporization point of water and other vaporizable substances thereby removing the surface of the tissue in said selected area.

25. The device of claim 24, wherein the probe forms a micropore in the surface of the tissue approximately 1–1000 .mu.m in diameter.

26. The device of claim 23, wherein the probe comprises at least one electrically heated probe.

27. The device of claim 26, and further comprising at least two conductors embedded in the tissue-contacting layer and at least one electrically heatable element connected to the conductors for supplying electric current to the at least one electrically heatable element.

28. The device of claim 23, wherein the probe comprises a target portion on the tissue-contacting layer which is responsive to optical energy so as to heat up and conduct heat to the tissue.

29. The device of claim 28, wherein the target portion comprises a quantity of photosensitizing material, and a carrier which is combined with the photosensitizing material such that the photosensitizing material is substantially uniformly dissolved or suspended therein, wherein the tissue-contacting layer serves as a substrate for the carrier-photosensitizing material combination.

30. The device of claim 28, wherein the tissue-contacting layer comprises a film material, and wherein the target portion comprises a substantially uniform suspension of photosensitizing material in the film material.

31. The device of claim 23, wherein the detecting layer comprises an electrochemical biosensor which is responsive to a level of glucose in interstitial fluid.

32. The device of claim 31, and further comprising a meter-interface layer comprising electrical contacts connected to the electrodes of the electrochemical biosensor, and which electrical contacts are suitable for connection to a meter.

33. The device of claim 23, wherein the detecting layer comprises a colorimetric sensor which provides an indication of glucose level in interstitial fluid.

34. The device of claim 33, end further comprising a meter-interface layer having a portion thereof which is transparent to optical energy.

35. The device of claim 23, and further comprising a mechanical element suitable for pressing the device onto a surface of the tissue to cause the surface of the tissue to bulge into an opening of the device proximate the probe.

36. The device of claim 23, and further comprising sealing means for pneumatically sealing the device to the surface of the tissue and forming a sealed chamber above the device; and means coupled to the sealing means for supplying negative pressure to the sealed chamber.

37. The system of claim 36, and further comprising a sealed electrical connection to the detecting layer and/or probe via the sealing means.

38. The device of claim 23, and further defining a fluid management chamber in a region of the device between the tissue-contacting layer and the detecting layer, wherein surfaces in the fluid management chamber are treated with a chemical substance so as to facilitate the flow of biological fluid to the detecting layer.

39. The device of claim 23, and further comprising a fluid-transporting layer between the tissue-contacting layer and the detecting, and in fluid communication with the detecting layer.

40. The device of claim 39, wherein fluid-transporting layer comprises a mesh material capable of wicking biological fluid.

41. The device of claim 39, wherein the fluid-transporting layer is treated with a chemical substance to enhance wicking capabilities of interstitial fluid.

42. The device claim 39, wherein the fluid-transporting layer is treated with a surfactant.

43. The device of claim 23, and further comprising an overcoat layer which overlies the tissue-contacting layer.

44. The device or claim 23, and further comprising means for coupling sonic energy through the device to the tissue.

45. The device of claim 44, and further comprising control means for controlling parameters of the sonic energy so that the sonic energy is adjusted to optimize each stage of a microporation, harvesting and analysis process.

46. A glucose monitoring system comprising: a poration/assay carriage supporting a poration head comprising at least one electrically heated probe, and a assay strip; a vacuum chamber mechanism for engaging a tissue surface and applying a vacuum in a chamber in which the poration/assay carriage is supported; means for supplying electrical current to the poration head so as to heat the electrically heated probe to form at least one micropore in the surface of the tissue; means for moving the poration/assay carriage with respect to the surface of the tissue so as to contact the assay strip with a bolus of biological fluid collected form the surface of the tissue; and means for interfacing with the assay strip to obtain a measurement of a characteristic of the biological fluid.

47. The system of claim 46, wherein the poration/assay carriage comprises a poration head having a plurality of electrically heated probes thereon.

48. A assay cartridge comprising: a plurality of assay elements, wherein each assay element comprises: a heated probe surface suitable for forming micropores when placed in contact with tissue; a fluid accumulation area adjacent the heated probe surface suitable for accumulating biological fluid on the surface of the tissue; and an assay area suitable for receiving a bolus of biological fluid from the fluid accumulation area to enable measurement or a characteristic of the biological fluid.

49. A glucose monitoring system comprising: a poration/assay carriage supporting a poration head comprising at least one electrically heated probe, and a assay strip; a vacuum chamber mechanism for engaging a tissue surface and applying a vacuum in chamber in which the poration/assay carriage is supported; means for supplying electrical current to the poration head so as to heat the electrically heated probe to form at least one micropore in the surface of the tissue; means for moving the poration/assay carriage with respect to the surface of the tissue so as to contact the assay strip with a bolus of biological fluid collected form the surface of the tissue; and means for interfacing with the assay strip to obtain a measurement of a characteristic of the biological fluid and further including a plurality as assay elements, wherein each assay element comprises: a heated probe surface suitable or forming micopores when placed in contact with tissue; a fluid accumulation area adjacent the heated probe surface suitable for accumulating biological fluid on the surface of the tissue; and an assay area suitable for receiving a bolus of biological fluid from the fluid accumulation area to enable measurement of a characteristic of the biological fluid and further including means for rotating the cartridge so as to contact each of the assay element during the microporation, harvesting and analysis process.

50. An integrated poration, harvesting and analysis device, comprising: (a) a tissue-contacting layer having a hole therethrough to permit a porator to create at least one opening in the tissue; and (b) a detecting layer in fluid communication with the at least one opening formed in the surface of the tissue, the detecting layer being responsive to a biological fluid collected from the tissue to provide an indication of a characteristic of the biological fluid.

51. An integrated poration, harvesting and analysis device, comprising: a) a tissue-contacting layer having a probe thereon suitable for conducting heat to a surface of a tissue to form at least one opening therein; and (b) a detecting layer in fluid communication with the at least one opening formed in the surface of the tissues, the detecting layer being responsive to a biological fluid collected from the tissue to provide an indication of a characteristic of the biological fluid and wherein surface portions of the tissue-contacting layer are coated with hydrophobic substances.

52. An integrated poration, harvesting and analysis device, comprising: (a) a tissue-contacting layer having a probe thereon suitable for conducting heat to a surface of a tissue to form at least one opening therein; and (b) a detecting layer in fluid communication with the at least one opening formed in the surface of the tissue, the detecting layer being responsive to a biological fluid collected from the tissue to provide an indication of a characteristic of the biological fluid and further comprising a sense electrode coupled to the detecting layer to facilitate determination that the detecting layer is sufficiently wetted with biological fluid.

\* \* \* \* \*